US012723075B2

(12) United States Patent
Laterra et al.

(10) Patent No.: US 12,723,075 B2
(45) Date of Patent: Sep. 1, 2026

(54) HUMANIZED ANTIBODIES DIRECTED AGAINST KCNK9

(71) Applicants: The Johns Hopkins University, Baltimore, MD (US); UNIVERSITY OF MARYLAND, BALTIMORE, Baltimore, MD (US); THE KENNEDY KRIEGER INSTITUTE, INC., Baltimore, MD (US)

(72) Inventors: John J. Laterra, Baltimore, MD (US); Amy M. Fulton, Baltimore, MD (US)

(73) Assignees: THE JOHNS HOPKINS UNIVERSITY, Baltimore, MD (US); UNIVERSITY OF MARYLAND, BALTIMORE, Baltimore, MD (US); THE KENNEDY KRIEGER INSTITUTE, INC., Baltimore, MD (US)

( * ) Notice: Subject to any disclaimer, the term of this patent is extended or adjusted under 35 U.S.C. 154(b) by 940 days.

(21) Appl. No.: 17/928,996

(22) PCT Filed: Jun. 3, 2021

(86) PCT No.: PCT/US2021/035610

§ 371 (c)(1),
(2) Date: Dec. 1, 2022

(87) PCT Pub. No.: WO2021/247805

PCT Pub. Date: Dec. 9, 2021

(65) Prior Publication Data

US 2023/0220067 A1 Jul. 13, 2023

Related U.S. Application Data

(60) Provisional application No. 63/035,093, filed on Jun. 5, 2020.

(51) Int. Cl.

| | |
|---|---|
| ***C07K 16/28*** | (2006.01) |
| ***A61K 39/395*** | (2006.01) |
| ***A61P 35/00*** | (2006.01) |
| ***C07K 16/30*** | (2006.01) |
| ***C12N 15/13*** | (2006.01) |
| *A61K 39/00* | (2006.01) |

(52) U.S. Cl.

CPC .............. *C07K 16/28* (2013.01); *A61P 35/00* (2018.01); *C07K 16/30* (2013.01); *A61K 2039/505* (2013.01); *C07K 2317/24* (2013.01); *C07K 2317/41* (2013.01); *C07K 2317/732* (2013.01)

(58) Field of Classification Search

CPC .... C07K 16/28; C07K 16/30; C07K 2317/24; C07K 2317/41; C07K 2317/732; A61P 35/00; A61K 2039/505; A61K 39/39558

See application file for complete search history.

(56) References Cited

U.S. PATENT DOCUMENTS

| | | | |
|---|---|---|---|
| 4,816,567 | A | 3/1989 | Cabilly et al. |
| 4,828,981 | A | 5/1989 | Maggio |
| 5,034,506 | A | 7/1991 | Summerton et al. |
| 5,585,089 | A | 12/1996 | Queen et al. |
| 5,693,761 | A | 12/1997 | Queen et al. |
| 5,693,762 | A | 12/1997 | Queen et al. |
| 6,180,370 | B1 | 1/2001 | Queen et al. |
| 7,022,500 | B1 | 4/2006 | Queen et al. |
| 8,568,992 | B2 | 10/2013 | Walker et al. |
| 9,663,782 | B2 | 5/2017 | Yu et al. |
| 2009/0028851 | A1 | 1/2009 | Stuhmer et al. |
| 2015/0315293 | A1 | 11/2015 | Damelin et al. |
| 2017/0342160 | A1 | 11/2017 | Mertens et al. |
| 2018/0092977 | A1 | 4/2018 | Laterra et al. |

FOREIGN PATENT DOCUMENTS

| | | |
|---|---|---|
| WO | WO 2015/010114 | 1/2015 |
| WO | WO 2016/149621 | 9/2016 |

OTHER PUBLICATIONS

Fu et al., Signal Transduction and Targeted Therapy, 7:93, pp. 1-25. (Year: 2022).*
Carter et al., Endocrine-Related Cancer, 11:659-687. (Year: 2004).*
Kovacs, I. et al. TASK-3 immunoreactivity shows differential distribution in the human gastrointestinal tract. Virchows Arch. Apr. 2005;446(4):402-10.
Extended European Search Report for EP 21817282.3, mailed Jun. 25, 2024, 9 pages.
International Search Report and Written Opinion for PCT/US21/35610. Mailed Oct. 27, 2021. 15 pages.
Abramovits et al., Sulfur/sodium sulfacetamide preparations. Skinmed. Mar.-Apr. 2004;3(2):95-101.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Apgar et al., Beyond CDR-grafting: Structure-guided humanization of framework and CDR regions of an anti-myostatin antibody. MAbs. Oct. 2016;8(7):1302-1318.
Arcangeli et al., Novel perspectives in cancer therapy: Targeting ion channels. Drug Resist Updat. Jul.-Aug. 2015;21-22:11-9.

(Continued)

*Primary Examiner* — Hong Sang
(74) *Attorney, Agent, or Firm* — Casimir Jones, SC; Thomas A. Isenbarger

(57) ABSTRACT

Provided herein are humanized monoclonal antibodies that bind to potassium two pore domain channel subfamily K member 9 (KCNK9). The humanized monoclonal antibodies comprise (a) a heavy chain variable region comprising an amino acid sequence of SEQ ID NO: 9, SEQ ID NO: 10, SEQ ID NO: 11, SEQ ID NO: 12, or SEQ ID NO: 13; and (b) a light chain variable region comprising an amino acid sequence of SEQ ID NO: 14, SEQ ID NO: 15, or SEQ ID NO: 16. Methods of using the antibodies to inhibit the growth of KCNK9-expressing cells also are provided.

17 Claims, 13 Drawing Sheets

Specification includes a Sequence Listing.

(56) References Cited

OTHER PUBLICATIONS

Arcangeli. Ion channels and transporters in cancer. 3. Ion channels in the tumor cell-microenvironment cross talk. Am J Physiol Cell Physiol. Oct. 2011;301(4):C762-71.
Arnould et al., Trastuzumab-based treatment of HER2-positive breast cancer: an antibody-dependent cellular cytotoxicity mechanism? Br J Cancer. Jan. 30, 2006;94(2):259-67.
Baer et al., An engineered human antibody fab fragment specific for Pseudomonas aeruginosa PcrV antigen has potent antibacterial activity. Infect Immun. Mar. 2009;77(3):1083-90.
Barel et al., Maternally inherited Birk Barel mental retardation dysmorphism syndrome caused by a mutation in the genomically imprinted potassium channel KCNK9. Am J Hum Genet. Aug. 2008;83(2):193-9.
Bazin-Redureau et al., Pharmacokinetics of heterologous and homologous immunoglobulin G, F(ab')2 and Fab after intravenous administration in the rat. J Pharm Pharmacol. Mar. 1997;49(3):277-81.
Becchetti. Ion channels and transporters in cancer. 1. Ion channels and cell proliferation in cancer. Am J Physiol Cell Physiol. Aug. 2011;301(2):C255-65.
Becker et al., Protection from graft-versus-host disease by HIV-1 envelope protein gp120-mediated activation of human CD4+ CD25+ regulatory T cells. Blood. Aug. 6, 2009;114(6):1263-9.
Berg et al., Motoneurons express heteromeric TWIK-related acid-sensitive K+ (Task) channels containing TASK-1 (KCNK3) and TASK-3 (KCNK9) subunits. J Neurosci. Jul. 28, 2004;24(30):6693-702.
Bhattacharyya et al., Nanoconjugation modulates the trafficking and mechanism of antibody induced receptor endocytosis. Proc Natl Acad Sci U S A. Aug. 17, 2010;107(33):14541-6.
Biegert et al., Sequence context-specific profiles for homology searching. Proc Natl Acad Sci U S A. Mar. 10, 2009;106(10):3770-5.
Bittner et al., From the background to the spotlight: TASK channels in pathological conditions. Brain Pathol. Nov. 2010;20(6):999-1009.
Bowers et al., Humanization of antibodies using heavy chain complementarity-determining region 3 grafting coupled with in vitro somatic hypermutation. J Biol Chem. Mar. 15, 2013;288(11):7688-7696.
Braasch et al., Novel antisense and peptide nucleic acid strategies for controlling gene expression. Biochemistry. Apr. 9, 2002;41(14):4503-10.
Braitbard et al., Competition between bound and free peptides in an ELISA-based procedure that assays peptides derived from protein digests. Proteome Sci. May 31, 2006;4:12. 14 pages.
Brash et al., Strontium phosphate transfection of human cells in primary culture: stable expression of the simian virus 40 large-T-antigen gene in primary human bronchial epithelial cells. Mol Cell Biol. May 1987;7(5):2031-4.
Butler et al., Integrating single-cell transcriptomic data across different conditions, technologies, and species. Nat Biotechnol. Jun. 2018;36(5):411-420.
Cheng et al., STIM1 plays an important role in TGF-β-induced suppression of breast cancer cell proliferation. Oncotarget. Mar. 29, 2016;7(13):16866-78.
Chou et al., Quantitative analysis of dose-effect relationships: the combined effects of multiple drugs or enzyme inhibitors. Adv Enzyme Regul. 1984;22:27-55.
Clackson et al., Making antibody fragments using phage display libraries. Nature. Aug. 15, 1991;352(6336):624-8.
Coburn et al., Discovery of a pharmacologically active antagonist of the two-pore-domain potassium channel K2P9.1 (TASK-3). ChemMedChem. Jan. 2, 2012;7(1):123-33.
Comes et al., Involvement of potassium channels in the progression of cancer to a more malignant phenotype. Biochim Biophys Acta. Oct. 2015;1848(10 Pt B):2477-92.
D'Amico et al., Potassium channels: novel emerging biomarkers and targets for therapy in cancer. Recent Pat Anticancer Drug Discov. Jan. 1, 2013;8(1):53-65.
Dobson. Gene therapy progress and prospects: magnetic nanoparticle-based gene delivery. Gene Ther. Feb. 2006;13(4):283-7.
Dookeran et al., Associations of two-pore domain potassium channels and triple negative breast cancer subtype in The Cancer Genome Atlas: systematic evaluation of gene expression and methylation. BMC Res Notes. Sep. 12, 2017;10(1):475. 9 pages.
Enyedi et al., Molecular background of leak K+ currents: two-pore domain potassium channels. Physiol Rev. Apr. 2010;90(2):559-605.
Ewert et al., Biophysical properties of human antibody variable domains. J Mol Biol. Jan. 17, 2003;325(3):531-53.
Fang et al., Effect of Fc-Glycan Structure on the Conformational Stability of IgG Revealed by Hydrogen/Deuterium Exchange and Limited Proteolysis. Biochemistry. Feb. 16, 2016;55(6):860-8.
Felipe et al., Potassium channels: new targets in cancer therapy. Cancer Detect Prev. 2006;30(4):375-85.
Feng et al., New insights into store-independent Ca(2+) entry: secretory pathway calcium ATPase 2 in normal physiology and cancer. Int J Oral Sci. Jun. 2013;5(2):71-4.
Gerdes et al., GA201 (RG7160): a novel, humanized, glycoengineered anti-EGFR antibody with enhanced ADCC and superior in vivo efficacy compared with cetuximab. Clin Cancer Res. Mar. 1, 2013;19(5):1126-38.
Haghverdi et al., Diffusion pseudotime robustly reconstructs lineage branching. Nat Methods. Oct. 2016;13(10):845-8.
Hahn et al., Translating Treg Therapy in Humanized Mice. Front Immunol. Dec. 14, 2015;6:623. 10 pages.
Heinrichs et al., Regulatory T-Cell Therapy for Graft-versus-host Disease. J Immunol Res Ther. 2016;1(1):1-14.
Holliger et al., Engineered antibody fragments and the rise of single domains. Nat Biotechnol. Sep. 2005;23(9):1126-36.
Honegger et al., The influence of the framework core residues on the biophysical properties of immunoglobulin heavy chain variable domains. Protein Eng Des Sel. Mar. 2009;22(3):121-34.
Hou et al., Humanization of an anti-CD34 monoclonal antibody by complementarity-determining region grafting based on computer-assisted molecular modelling. J Biochem. Jul. 2008;144(1):115-20.
Hsu et al., Complement activation mediates cetuximab inhibition of non-small cell lung cancer tumor growth in vivo. Mol Cancer. Jun. 7, 2010;9:139. 8 pages.
Innamaa et al., Expression and prognostic significance of the oncogenic K2P potassium channel KCNK9 (TASK-3) in ovarian carcinoma. Anticancer Res. Apr. 2013;33(4):1401-8.
Jemal et al., Global cancer statistics. CA Cancer J Clin. Mar.-Apr. 2011;61(2):69-90.
Johnston. Biolistic transformation: microbes to mice. Nature. Aug. 23, 1990;346(6286):776-7.
Junttila et al., Superior in vivo efficacy of afucosylated trastuzumab in the treatment of HER2-amplified breast cancer. Cancer Res. Jun. 1, 2010;70(11):4481-9.
Kapoor. TASK3 and its role in neuro and systemic oncogenesis. J Neurooncol. Jun. 2008;88(2):243.
Kashmiri et al., SDR grafting—a new approach to antibody humanization. Methods. May 2005;36(1):25-34.
Kitts et al., A method for producing recombinant baculovirus expression vectors at high frequency. Biotechniques. May 1993;14(5):810-7.
Knappik et al., Fully synthetic human combinatorial antibody libraries (HuCAL) based on modular consensus frameworks and CDRs randomized with trinucleotides. J Mol Biol. Feb. 11, 2000;296(1):57-86.
Köhler et al., Derivation of specific antibody-producing tissue culture and tumor lines by cell fusion. Eur J Immunol. Jul. 1976;6(7):511-9.
Konishi et al., Utilization of complement-dependent cytotoxicity to measure low levels of antibodies: application to nonstructural protein 1 in a model of Japanese encephalitis virus. Clin Vaccine Immunol. Jan. 2008;15(1):88-94.
Kosztka et al., Inhibition of TASK-3 (KCNK9) channel biosynthesis changes cell morphology and decreases both DNA content and

(56) References Cited

OTHER PUBLICATIONS mitochondrial function of melanoma cells maintained in cell culture. Melanoma Res. Aug. 2011;21(4):308-22.
Kügler et al., Stabilization and humanization of a single-chain Fv antibody fragment specific for human lymphocyte antigen CD19 by designed point mutations and CDR-grafting onto a human framework. Protein Eng Des Sel. Mar. 2009;22(3):135-47.
Lazar et al., A molecular immunology approach to antibody humanization and functional optimization. Mol Immunol. Mar. 2007;44(8):1986-98.
Lehen'Kyi et al., Ion channels and transporters in cancer. 5. Ion channels in control of cancer and cell apoptosis. Am J Physiol Cell Physiol. Dec. 2011;301(6):C1281-9.
Linden et al., K+ channel TASK-1 knockout mice show enhanced sensitivities to ataxic and hypnotic effects of GABA(A) receptor ligands. J Pharmacol Exp Ther. Oct. 2008;327(1):277-86.
Litan et al., Cancer as a channelopathy: Ion channels and pumps in tumor development and progression. Front Cell Neurosci. Mar. 17, 2015;9:86. 11 pages.
Liu et al., Afucosylated antibodies increase activation of FcyRIIIa-dependent signaling components to intensify processes promoting ADCC. Cancer Immunol Res. Feb. 2015;3(2):173-83.
Lonberg. Human antibodies from transgenic animals. Nat Biotechnol. Sep. 2005;23(9):1117-25.
Lu et al., Fluorescence-Based Measurements of Store-Operated Ca2+ Entry in Cancer Cells Using Fluo-4 and Confocal Live-Cell Imaging. Methods Mol Biol. 2018;1843:63-68.
Luckow et al., Efficient generation of infectious recombinant baculoviruses by site-specific transposon-mediated insertion of foreign genes into a baculovirus genome propagated in *Escherichia coli*. J Virol. Aug. 1993;67(8):4566-79.
Luckow. Baculovirus systems for the expression of human gene products. Curr Opin Biotechnol. Oct. 1993;4(5):564-72.
Machaca. Ca(2+) signaling, genes and the cell cycle. Cell Calcium. Nov. 2010;48(5):243-50.
Mao et al., Fast protein sequencing of monoclonal antibody by real-time digestion on emitter during nanoelectrospray. MAbs. May/Jun. 2019;11(4):767-778.
Marks et al., By-passing immunization. Human antibodies from V-gene libraries displayed on phage. J Mol Biol. Dec. 5, 1991;222(3):581-97.
Medhurst et al., Distribution analysis of human two pore domain potassium channels in tissues of the central nervous system and periphery. Mol Brain Res. Jan. 31, 2001;86(1-2):101-14.
Mendelsohn. Epidermal growth factor receptor inhibition by a monoclonal antibody as anticancer therapy. Clin Cancer Res. Dec. 1997;3(12 Pt 2):2703-7.
Meuth et al., The two-pore domain potassium channel TASK3 functionally impacts glioma cell death. J Neurooncol. May 2008;87(3):263-70.
Molina et al., Trastuzumab (herceptin), a humanized anti-Her2 receptor monoclonal antibody, inhibits basal and activated Her2 ectodomain cleavage in breast cancer cells. Cancer Res. Jun. 15, 2001;61(12):4744-9.
Mu et al., Genomic amplification and oncogenic properties of the KCNK9 potassium channel gene. Cancer Cell. Mar. 2003;3(3):297-302.
Mulkey et al., TASK channels determine pH sensitivity in select respiratory neurons but do not contribute to central respiratory chemosensitivity. J Neurosci. Dec. 19, 2007;27(51):14049-58.
Mutis et al., Human regulatory T cells control xenogeneic graft-versus-host disease induced by autologous T cells in RAG2-/-gammac-/-immunodeficient mice. Clin Cancer Res. Sep. 15, 2006;12(18):5520-5.
Niwa et al., Defucosylated chimeric anti-CC chemokine receptor 4 IgG1 with enhanced antibody-dependent cellular cytotoxicity shows potent therapeutic activity to T-cell leukemia and lymphoma. Cancer Res. Mar. 15, 2004;64(6):2127-33.
Okazaki et al., Fucose depletion from human IgG1 oligosaccharide enhances binding enthalpy and association rate between IgG1 and FcgammaRIIIa. J Mol Biol. Mar. 5, 2004;336(5):1239-49.
Overdijk et al., Crosstalk between human IgG isotypes and murine effector cells. J Immunol. Oct. 1, 2012;189(7):3430-8.
Pardo et al., The roles of K(+) channels in cancer. Nat Rev Cancer. Jan. 2014;14(1):39-48.
Patel et al., The 2P-domain K+ channels: role in apoptosis and tumorigenesis. Pflugers Arch—Eur J Physiol. Jun. 2004;448(3):261-73.
Pei et al., Oncogenic potential of TASK3 (Kcnk9) depends on K+ channel function. Proc Natl Acad Sci U S A. Jun. 24, 2003;100(13):7803-7.
Presta et al., Engineering therapeutic antibodies for improved function. Biochem Soc Trans. Aug. 2002;30(4):487-90.
Prevarskaya et al., Ion channels and the hallmarks of cancer. Trends Mol Med. Mar. 2010;16(3):107-21.
Queen et al., A humanized antibody that binds to the interleukin 2 receptor. Proc Natl Acad Sci U S A. Dec. 1989;86(24):10029-33.
Riechmann et al., Reshaping human antibodies for therapy. Nature. Mar. 24, 1988;332(6162):323-7.
Ritter et al., Serological analysis of human anti-human antibody responses in colon cancer patients treated with repeated doses of humanized monoclonal antibody A33. Cancer Res. Sep. 15, 2001;61(18):6851-9.
Scallon et al., Quantitative in vivo comparisons of the Fc gamma receptor-dependent agonist activities of different fucosylation variants of an immunoglobulin G antibody. Int Immunopharmacol. Jun. 2007;7(6):761-72.
Shields et al., Lack of fucose on human IgG1 N-linked oligosaccharide improves binding to human Fcgamma RIII and antibody-dependent cellular toxicity. J Biol Chem. Jul. 26, 2002;277(30):26733-40.
Shinkawa et al., The absence of fucose but not the presence of galactose or bisecting N-acetylglucosamine of human IgG1 complex-type oligosaccharides shows the critical role of enhancing antibody-dependent cellular cytotoxicity. J Biol Chem. Jan. 31, 2003;278(5):3466-73.
Shultz et al., Human lymphoid and myeloid cell development in NOD/LtSz-scid IL2R gamma null mice engrafted with mobilized human hemopoietic stem cells. Blood. 2004; 104(11):248.
Shultz et al., Human lymphoid and myeloid cell development in NOD/LtSz-scid IL2R gamma null mice engrafted with mobilized human hemopoietic stem cells. J Immunol. May 15, 2005;174(10):6477-89.
Siegel et al., Cancer statistics, 2013. CA Cancer J Clin. Jan. 2013;63(1):11-30.
Söding. Protein homology detection by HMM-HMM comparison. Bioinformatics. Apr. 1, 2005;21(7):951-60.
Stavenhagen et al., Fc optimization of therapeutic antibodies enhances their ability to kill tumor cells in vitro and controls tumor expansion in vivo via low-affinity activating Fcgamma receptors. Cancer Res. Sep. 15, 2007;67(18):8882-90.
Sun et al., A monoclonal antibody against KCNK9 K(+) channel extracellular domain inhibits tumour growth and metastasis. Nat Commun. Feb. 4, 2016;7:10339. 12 pages.
Sun et al., Abstract 640: Probing the tumorigenic properties of two pore potassium channels using inhibitory anti-KCNK9 mAbs. Cancer Res. 2015, 75(15) 640-75.
Sun et al., STIM1- and Orai1-mediated Ca(2+) oscillation orchestrates invadopodium formation and melanoma invasion. J Cell Biol. Nov. 24, 2014;207(4):535-48.
Urlaub et al., Isolation of Chinese hamster cell mutants deficient in dihydrofolate reductase activity. Proc. Natl. Acad. Sci. USA. 1980, 77(7) : 4216-4220.
Villalonga et al., Potassium channels are a new target field in anticancer drug design. Recent Pat Anticancer Drug Discov. Nov. 2007;2(3):212-23.
Wahlestedt et al., Potent and nontoxic antisense oligonucleotides containing locked nucleic acids. Proc Natl Acad Sci U S A. May 9, 2000;97(10):5633-8.

(56) References Cited

OTHER PUBLICATIONS

Walser et al., Immune-mediated modulation of breast cancer growth and metastasis by the chemokine Mig (CXCL9) in a murine model. J Immunother. Jul.-Aug. 2007;30(5):490-8.
Wang et al., Cyclohexene nucleic acids (CeNA): serum stable oligonucleotides that activate RNase H and increase duplex stability with complementary Rna. J. Am. Chem. Soc. 2000, 122, 8595-8602.
Wang et al., Single-Cell Co-expression Analysis Reveals Distinct Functional Modules, Co-regulation Mechanisms and Clinical Outcomes. PLoS Comput Biol. Apr. 21, 2016;12(4):e1004892. 18 pages.
Weaver et al., A thallium-sensitive, fluorescence-based assay for detecting and characterizing potassium channel modulators in mammalian cells. J Biomol Screen. Dec. 2004;9(8):671-7.
Whitsett et al., Molecular determinants of lung cancer metastasis to the central nervous system. Transl Lung Cancer Res. Aug. 2013;2(4):273-83.
Wonderlin et al., Changes in membrane potential during the progression of MCF-7 human mammary tumor cells through the cell cycle. J Cell Physiol. Oct. 1995;165(1):177-85.
Yamane-Ohnuki et al., Production of therapeutic antibodies with controlled fucosylation. MAbs. May-Jun. 2009;1(3):230-6.
Yang et al., Membrane potential and cancer progression. Front Physiol. Jul. 17, 2013;4:185. 10 pages.
Yu et al., Antibody-membrane switch (AMS) technology for facile cell line development. Protein Eng Des Sel. Oct. 2014;27(10):309-15.
Zhang et al., Potassium channels and proliferation and migration of breast cancer cells. Acta Physiologica Sinica, Feb. 25, 2009, 61(1): 15-20.
Zheng et al., The impact of glycosylation on monoclonal antibody conformation and stability. MAbs. Nov.-Dec. 2011;3(6):568-76.
Zúñiga et al., TASK-3 Downregulation Triggers Cellular Senescence and Growth Inhibition in Breast Cancer Cell Lines. Int J Mol Sci. Mar. 29, 2018;19(4):1033. 17 pages.

* cited by examiner

* with control (p<0.0001)
with AZD2461 (P<0.0001)
+ with KCNK9Ab (p<0.0001)

* with control (0.0004)
with Palbociclib (P<0.0031)
+ with KCNK9Ab (p<0.0006)

HUMANIZED ANTIBODIES DIRECTED AGAINST KCNK9

This application is a national phase application under 35 U.S.C. § 371 of PCT International Application No.: PCT/US2021/035610, filed on Jun. 3, 2021, which claims the benefit of U.S. Provisional Patent Application No. 63/035,093, filed Jun. 5, 2020, the contents of each of which are incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 12,483 Byte ASCII (Text) file named "38269-601_ST25.txt," created on Jun. 3, 2021.

BACKGROUND

The role of $K^+$ channels in tumorigenesis has been recognized for over a decade (Villalonga, *Recent Pat Anticancer Drug Discov,* 2: 212-23 (2007); Meuth, *J Neurooncol,* 87: 263-70 (2008); Zhang, *Sheng Li Xue Bao,* 61:15-20 (2009); Bittner, *Brain Pathol,* 20: 999-1009 (2010); Becchetti, *Am J Physiol Cell Physiol,* 301: C255-65 (2011); Arcangeli, *Am J Physiol Cell Physiol,* 301: C762-71 (2011); Lehen'kyi, *Am J Physiol Cell Physiol,* 301: C1281-9 (2011); D'Amico, *Recent Pat Anticancer Drug Discov,* 8: 53-65 (2013); Innamaa, *Anticancer Res,* 33: 1401-8 (2013); reviewed by Felipe, *Cancer Detect Prev.,* 30: 375-85 (2006); Prevarskaya, *Trends Mol Med,* 16: 107-21 (2010); Pardo, *Nature Reviews Cancer,* 14: 39-48 (2014); Litan, *Front Cell Neurosci,* 9: 86 (2015)). In particular, the two pore domain channel subfamily K member 9, KCNK9, exerts a tumorigenic and pro-metastatic effect in several models. Furthermore, KCNK9 is genetically-amplified and overexpressed from 5- to >100-fold in almost 50% of breast cancers, 33% of lung cancers, and 25% of ovarian cancers (Mu et al., *Cancer Cell,* 3: 297-302 (2003)). In xenograft models, tumor cells over-expressing KCNK9 are aggressive, and a dominant-negative mutant of KCNK9 abolishes its $K^+$ channel activity and abrogates its oncogenic function, without any effect on normal cell growth (Pei et al., *Proc Natl Acad Sci USA,* 100: 7803-7807 (2003)). Similarly, short hairpin RNA (shRNA) knock-down of KCNK9 decreased metabolic activity and growth of melanoma cells (Kosztka et al., *Melanoma Res,* 21: 308-322 (2011)). These data support the hypothesis that KCNK9 promotes tumor growth and may be a therapeutic target in KCNK9-stratified malignancies. Despite the data highlighting the potential of KCNK9-directed therapeutics, a lack of specific reagents has hindered both basic research and preclinical studies.

There remains a need for compositions and methods that inhibit KCNK9 activity in KCNK9-expressing cancer cells.

BRIEF SUMMARY OF THE INVENTION

The disclosure provides a humanized antibody or an antigen-binding fragment thereof which specifically binds to potassium two pore domain channel subfamily K member 9 (KCNK9), which humanized antibody comprises: (a) a heavy chain variable region comprising an amino acid sequence of SEQ ID NO: 9, SEQ ID NO: 10, SEQ ID NO: 11, SEQ ID NO: 12, or SEQ ID NO: 13; and (b) a light chain variable region comprising an amino acid sequence of SEQ ID NO: 14, SEQ ID NO: 15, or SEQ ID NO: 16.

The disclosure also provides compositions and kits comprising the aforementioned humanized antibody, as well as the use of the aforementioned humanized antibody to inhibit KCNK9 activity in a cell (e.g., a cancer cell).

BRIEF DESCRIPTION OF THE FIGURES

FIG. 1 includes flow cytometry images showing binding of chimeric and humanized KCNK9 antibodies to KCNK9-expressing HEK293 cells.

DETAILED DESCRIPTION OF THE INVENTION

Figure 1A:
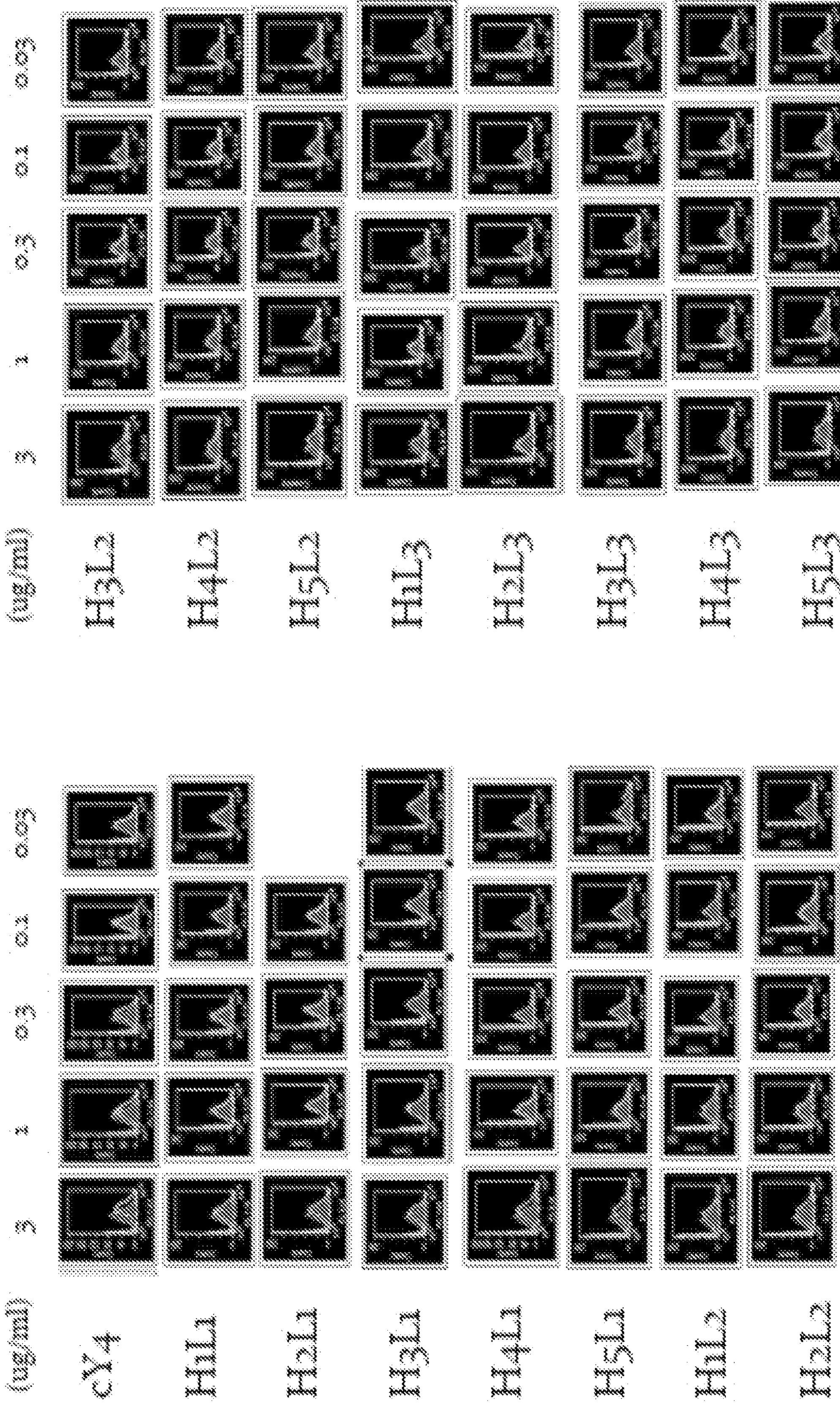
FIG. 1A includes images of chimeric and humanized KCNK9 monoclonal antibodies stained with anti-human Fc FITC secondary antibody.

The present disclosure is predicated, at least in part, on the generation of humanized monoclonal antibodies that bind with high affinity to KCNK9 expressed on the surface of cells and enhance antibody-dependent cellular cytotoxicity (ADCC). The humanized antibodies disclosed herein also inhibit the growth of different tumor types in vitro and in vivo.

Definitions

To facilitate an understanding of the present technology, a number of terms and phrases are defined below. Additional definitions are set forth throughout the detailed description.

The term "immunoglobulin" or "antibody," as used herein, refers to a protein that is found in blood or other bodily fluids of vertebrates, which is used by the immune system to identify and neutralize foreign objects, such as bacteria and viruses. Typically, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_{H1}$, $C_{H2}$, and $C_{H3}$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the CDRs. There are four framework regions in each variable domain, which are designated FR1, FR2, FR3, and FR4. The framework regions form the β sheets that provide the structural framework of the variable region (see, e.g., C. A. Janeway et al. (eds.), *Immunobiology,* 5th Ed., Garland Publishing, New York, N.Y. (2001)).

The framework regions are connected by three CDRs. As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

As used herein, when an antibody or other entity (e.g., antigen binding domain) "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

The terms "fragment of an antibody," "antibody fragment," and "antigen-binding fragment" of an antibody are used interchangeably herein to refer to one or more fragments of an antibody that retain the ability to specifically bind to an antigen (see, generally, Holliger et al., *Nat. Biotech.,* 23(9): 1126-1129 (2005)). Any antigen-binding fragment of the humanized antibody described herein is within the scope of the invention. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $C_{H1}$ domains, (ii) a F(ab')2 fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an F(ab')2 fragment using mild reducing conditions, (v) a disulfide-stabilized Fv fragment (dsFv), and (vi) a domain antibody (dAb), which is an antibody single variable region domain ($V_H$ or $V_L$) polypeptide that specifically binds antigen.

The term "chimeric" antibody, as used herein, refers to an antibody or fragment thereof comprising a non-human antigen binding region (variable domains of the heavy and light chains, $V_H$ and $V_L$) and a human constant domain. In contrast, a "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. Desirably, all of the CDRs of the heavy and light chain of a humanized antibody are derived or obtained from a non-human monoclonal antibody. A human antibody, a chimeric antibody, or a humanized antibody can be obtained by any suitable means, including via in vitro sources (e.g., a hybridoma or a cell line producing an antibody recombinantly) and in vivo sources (e.g., rodents). Methods for generating monoclonal antibodies are known in the art and are described in, for example, Köhler and Milstein, *Eur. J. Immunol.,* 5: 511-519 (1976); Harlow and Lane (eds.), Antibodies: A Laboratory Manual, CSH Press (1988); and Janeway et al. (eds.), *Immunobiology,* 5th Ed., Garland Publishing, New York, N.Y. (2001)). Methods for generating humanized antibodies are known in the art (see, e.g., An, Z. (ed.), *Therapeutic Monoclonal Antibodies: From Bench to Clinic*, John Wiley & Sons, Inc., Hoboken, N.J. (2009); and Apgar et al., *MAbs,* 8(7): 1302-1318 (2016)), and may include, e.g., grafting of non-human CDRs onto a human antibody scaffold (see, e.g., Kashmiri et al., *Methods,* 36(1): 25-34 (2005); and Hou et al., *J. Biochem.,* 144(1): 115-120 (2008); and U.S. Pat. Nos. 5,585,089; 5,693,761; 5,693,762; 6,180,370; and 7,022,500).

The terms "germline" and "germline gene segments," may be used interchangeably to refer to the genes from the germline (i.e., the haploid gametes and those diploid cells from which they are formed). Germline DNA contains multiple gene segments that encode a single immunoglobulin heavy or light chain. These gene segments are carried in the germ cells but cannot be transcribed and translated into heavy and light chains until they are arranged into functional genes. During B-cell differentiation in the bone marrow, these gene segments are randomly shuffled by a dynamic genetic system capable of generating more than one hundred specificities.

The terms "nucleic acid," "polynucleotide," "nucleotide sequence," and "oligonucleotide" are used interchangeably herein and refer to a polymer or oligomer of pyrimidine and/or purine bases, preferably cytosine, thymine, and uracil, and adenine and guanine, respectively (See Albert L. Lehninger, *Principles of Biochemistry*, at 793-800 (Worth Pub. 1982)). The terms encompass any deoxyribonucleotide, ribonucleotide, or peptide nucleic acid component, and any chemical variants thereof, such as methylated, hydroxymethylated, or glycosylated forms of these bases. The polymers or oligomers may be heterogenous or homogenous in composition, may be isolated from naturally occurring sources, or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see, e.g., Braasch and Corey, *Biochemistry,* 41(14): 4503-4510 (2002) and U.S. Pat. No. 5,034,506), locked nucleic acid (LNA; see Wahlestedt et al., *Proc. Natl. Acad. Sci. U.S.A.,* 97: 5633-5638 (2000)), cyclohexenyl nucleic acids (see Wang, *J. Am. Chem. Soc.,* 122: 8595-8602 (2000)), and/or a ribozyme. The terms "nucleic acid" and "nucleic acid sequence" may also encompass a chain comprising non-natural nucleotides, modified nucleotides, and/or non-nucleotide building blocks that can exhibit the same function as natural nucleotides (e.g., "nucleotide analogs").

The terms "peptide," "polypeptide," and "protein" are used interchangeably herein and refer to a polymeric form of amino acids of any length, which can include coded and non-coded amino acids, chemically or biochemically modified or derivatized amino acids, and polypeptides having modified peptide backbones.

The terms "immunogen" and "antigen" are used interchangeably herein and refer to any molecule, compound, or substance that induces an immune response in an animal (e.g., a mammal). An "immune response" can entail, for example, antibody production and/or the activation of immune effector cells. An antigen in the context of the disclosure can comprise any subunit, fragment, or epitope of any proteinaceous or non-proteinaceous (e.g., carbohydrate or lipid) molecule that provokes an immune response in a mammal. By "epitope" is meant a sequence of an antigen that is recognized by an antibody or an antigen receptor. Epitopes also are referred to in the art as "antigenic determinants." In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three-dimensional structural characteristics (e.g., a "conformational" epitope) and/or specific charge characteristics. The antigen can be a protein or peptide of viral, bacterial, parasitic, fungal, protozoan, prion, cellular, or extracellular origin, which provokes an immune response in a mammal, preferably leading to protective immunity.

The term "tumor," as used herein, refers to an abnormal mass of tissue that results when cells divide more than they should or do not die when they should. In the context of the present disclosure, the term tumor may refer to tumor cells and tumor-associated stromal cells (as described above). Tumors may be benign and non-cancerous if they do not invade nearby tissue or spread to other parts of the organism. In contrast, the terms "malignant tumor," "cancer," and "cancer cells" may be used interchangeably herein and refer to a tumor comprising cells that divide uncontrollably and can invade nearby tissues. Cancer cells also can spread or "metastasize" to other parts of the body through the blood and lymph systems.

An agent is "cytotoxic" and induces "cytotoxicity" if the agent (e.g., the humanized antibody described herein) kills or inhibits the growth of cells, particularly cancer cells. In some embodiments, for example, cytotoxicity includes preventing cancer cell division and growth, as well as reducing the size of a tumor or cancer. Cytotoxicity of tumor cells may be measured using any suitable cell viability assay known in the art, such as, for example, assays which measure cell lysis, cell membrane leakage, and apoptosis. For example, methods including but not limited to trypan blue assays, propidium iodide assays, lactate dehydrogenase (LDH) assays, tetrazolium reduction assays, resazurin reduction assays, protease marker assays, 5-bromo-2'-deoxy-uridine (BrdU) assays, and ATP detection may be used. Cell viability assay systems that are commercially available also may be used and include, for example, CELLTITER-GLO® 2.0 (Promega, Madison, Wis.), VIVAFIX™ 583/603 Cell Viability Assay (Bio-Rad, Hercules, Calif.), and CYTOTOX-FLUOR™ Cytotoxicity Assay (Promega, Madison, Wis.).

Potassium Two Pore Domain Channel Subfamily K Member 9 (KCNK9)

Provided herein is a humanized antibody or an antigen-binding fragment thereof which specifically binds to KCNK9. KCNK9 is a member of the K2P channel family. Under physiological conditions, KCNK9 is primarily expressed in tissues of the central nervous system such as the cerebellum, acting to maintain resting membrane potential and regulate action potential firing (Enyedi & Czirjak, *Physiological Reviews,* 90: 559-605 (2010); and Medhurst et al., *Brain Res Mol Brain Res,* 86: 101-14 (2001)). KCNK9 channels generate outwardly rectifying currents that are modulated by a wide range of chemical and physical stimuli such as acidification and hypoxia. Thus, KCNK9 has the potential to transduce cancer-specific microenvironmental signals across cell membranes and thereby modulate cancer cell growth and survival. Indeed, KCNK9 has been implicated in cancer based on its genomic amplification, mRNA, and protein over-expression in human breast tumors and lung tumors (Mu et al., *Cancer Cell,* 3: 297-302 (2003)). Overexpression of KCNK9 has been shown to promote transformation of mouse embryonic fibroblasts in nude mice, possibly by improving cell survival under hypoxic or serum-deprived conditions (Mu et al., supra; Pei et al., *Proc Natl Acad Sci USA,* 100: 7803-7807 (2003)). Kcnk9 promoter hypomethylation also has been linked to KCNK9 over-expression in triple negative breast cancer (Dookeran et al., *BMC Res Notes,* 10: 475 (2017)).

The mechanism by which endogenous KCNK9 contributes to neoplasia and its potential as a therapeutic target has remained elusive due to the lack of specific modulators of KCNK9 functions. Genetic studies of K2P channels are often difficult to interpret due to developmental and compensatory effects (Linden et al., *Journal of Pharmacology and Experimental Therapeutics,* 327: 277-286 (2008)). High throughput screening of small molecules has been carried out to identify specific modulators of KCNK9, but limited progress has been made in this regard (Miller et al. (2012) *Probe Reports from the NIH Molecular Libraries Program*). The antibodies and related methods of use described herein address some of these concerns.

Antibodies

While KCNK9 antibodies are known in the art (see, e.g., Sun et al., Nat. Commun., 7: 10339 (2016)) and are commercially available from sources such as, for example, Abcam (Cambridge, Mass.), the present disclosure provides a novel humanized antibody or antigen-binding fragment thereof that specifically binds to KCNK9. The humanized antibody or antigen-binding fragment thereof desirably comprises (a) a heavy chain variable region comprising a CDR1 amino acid sequence of SEQ ID NO: 3, a CDR2 amino acid sequence of SEQ ID NO: 4, and a CDR3 amino acid sequence of SEQ ID NO: 5; and (b) a light chain variable region comprising a CDR1 amino acid sequence of SEQ ID NO: 6, a CDR2 amino acid sequence of SEQ ID NO: 7, and a CDR3 amino acid sequence of SEQ ID NO: 8.

Alternatively, the humanized antibody or antigen-binding fragment thereof may comprise heavy chain CDR1. CDR2, and CDR3 amino acid sequences that are at least 90% identical to SEQ ID NO: 3, SEQ ID NO: 4, and/or SEQ ID NO: 5, respectively, and/or light chain CDR1, CDR2, and CDR3 amino acid sequences that are at least 90° %6 identical to SEQ ID NO: 6, SEQ ID NO: 7, and/or SEQ ID NO: 8, respectively.

In one embodiment, (i) each of the heavy chain variable region CDR1, CDR2, and/or CDR3 amino acid sequences comprises, consists essentially of, or consists of SEQ ID NO: 3, SEQ ID NO: 4, and/or SEQ ID NO: 5, respectively, and (ii) each of the light chain variable region CDR1, CDR2, and/or CDR3 amino acid sequences comprises, consists essentially of, or consists of SEQ ID NO: 6, SEQ ID NO: 7, and/or SEQ ID NO: 8, respectively. When the heavy and/or light chain CDR1, CDR2, and CDR3 of the disclosed humanized antibody consists essentially of the amino acid sequences set forth above, additional components can be included in the CDR that do not materially affect the humanized antibody or antigen-binding fragment thereof (e.g., protein moieties such as biotin that facilitate purification or isolation). When the heavy and/or light chain CDR1, CDR2, and CDR3 of the disclosed humanized antibody consist of the amino acid sequences set forth above, each CDR does not comprise any additional components (i.e., components that are not endogenous to the CDR).

In some embodiments, the humanized antibody or antigen-binding fragment thereof comprises (a) a heavy chain variable region ($V_H$) amino acid sequence comprising, consisting essentially of, or consisting of any one of SEQ ID NO: 9, SEQ ID NO: 10, SEQ ID NO: 11, SEQ ID NO: 12, or SEQ ID NO: 13 and (b) a light chain variable region ($V_L$) amino acid sequence comprising, consisting essentially of, or consisting of any one of SEQ ID NO: 14, SEQ ID NO: 15, or SEQ ID NO: 16. When the $V_H$ amino acid sequence consists essentially of SEQ ID NO: 9, SEQ ID NO: 10, SEQ ID NO: 11, SEQ ID NO: 12, or SEQ ID NO: 13, additional components can be included in the heavy chain variable region that do not materially affect the antibody or antigen-binding fragment thereof (e.g., protein moieties such as biotin that facilitate purification or isolation). When the $V_H$ amino acid sequence consists of SEQ ID NO: 9, SEQ ID NO: 10, SEQ ID NO: 11, SEQ ID NO: 12, or SEQ ID NO: 13, the heavy chain variable region does not comprise any additional components (i.e., components that are not endogenous to the heavy chain variable region). Similarly, when the $V_L$ amino acid sequence consists essentially of SEQ ID NO: 14, SEQ ID NO: 15, or SEQ ID NO: 16, additional components can be included in the light chain variable region that do not materially affect the antibody or antigen-binding fragment thereof. When the $V_L$ amino acid sequence consists of SEQ ID NO: 14, SEQ ID NO: 15, or SEQ ID NO; 16, the light chain variable region does not comprise any additional components.

The above-described $V_H$ and $V_L$ amino acid sequences can be paired in any combination that provides for optimal binding to KCNK9 and maximum inhibition of KCNK9 activity. Exemplary antibody pairings include (a) a heavy chain variable region amino acid sequence of SEQ ID NO: 12 and a light chain variable region amino acid sequence of SEQ ID NO: 15; (b) a heavy chain variable region amino acid sequence of SEQ ID NO: 12 and a light chain variable region amino acid sequence of SEQ ID NO: 16; (c) a heavy chain variable region amino acid sequence of SEQ ID NO: 13 and a light chain variable region amino acid sequence of SEQ ID NO: 15; or (d) a heavy chain variable region amino acid sequence of SEQ ID NO: 13 and a light chain variable region amino acid sequence of SEQ ID NO: 16. Other combinations of $V_H$ and $V_L$ amino acid sequences are encompassed by the present disclosure, however.

The disclosure also provides an antibody or antigen-binding fragment thereof which comprises a heavy chain variable region amino acid sequence that is at least 90°/% identical (e.g., at least 91%, at least 92%, at least 93%, at least 94%, at least 95%, at least 96%, at least 97%, at least 98%, at least 99%, or 100% identical) to any one of SEQ ID NO: 9, SEQ ID NO: 10, SEQ ID NO: 11, SEQ ID NO: 12, or SEQ ID NO: 13 and a light chain variable region amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 14, SEQ ID NO: 15, or SEQ ID NO: 16. Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FAS™, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106(10): 3770-3775 (2009), Durbin et al., eds., *Biological Sequence Analysis: Probabilistic Models of Proteins and Nucleic Acids*, Cambridge University Press, Cambridge, UK (2009), *Soding, Bioinformatics,* 21(7): 951-960 (2005), Altschul et al., *Nucleic Acids Res.,* 25(17): 3389-3402 (1997), and Gusfield, Algorithms on Strings, Trees and Sequences, Cambridge University Press, Cambridge UK (1997)).

One or more amino acids of the aforementioned humanized antibody or antigen-fragment thereof can be replaced or substituted with a different amino acid. In some embodiments, for example, the humanized antibody comprises a least one amino acid substitution in the heavy chain framework region and/or at least one amino acid substitution in the light chain framework region Such framework amino acid substitutions desirably enhance the binding of the antibody to KCNK9, increase antibody-dependent cell-mediated cytotoxicity (ADCC), and/or increase cancer cell growth inhibition as compared to a humanized antibody lacking the at least one amino acid substitution.

As discussed above, antibody humanization may involve grafting non-human CDRs onto human acceptor framework regions, such as human acceptor germline framework regions. This method, however, leaves only the CDRs with xenogeneic residues (Queen et al., *Proc Natl Acad Sci USA,* 86:10029-33 (1989); Riechmann et al., *Nature,* 332: 323-7 (1988); Kahmiri et al., *Methods,* 36: 25-34 (2005); and Ritter et al., *Cancer Res,* 61: 6851-9 (2001)). To further minimize the foreign CDR content, humanization may involve methods that select for reduced foreign content in the humanization process and/or methods that remove the foreign content after CDR grafting. An additional humanization method includes screening for germline segments while only grafting the CDR3 of the heavy and light chain (Bayer et al., *Infect Immun,* 77: 1083-90 (2009)). This method can also be combined with affinity optimization using somatic hypermutation (Bowers et al., *J Biol Chem,* 288: 7688-96 (2013)). In other embodiments, immunologically relevant antibody humanness, or human string content, may be used to select humanized antibodies. Here, framework segments are selected from multiple germlines to make the overall variable region more humanlike (Lazar et al., *Mol Immunol,* 44: 1986-98 (2007)).

Human antibody variable domain consensus regions that may be used as human acceptor frameworks are known in the art (see, e.g., Ewert et al., *J Mol Biol,* 325: 531-53 (2003); and Knappik et al., *J. Mol. Biol.,* 296: 57-86 (2000)) and any such consensus domain may be employed as a heavy or light chain acceptor framework in the context of the present disclosure. In this regard, V-genes from the VH1, VH3 and VH5 families have been found to be better biotherapeutic candidates than those from other families (Ewert et al., supra). In some embodiments, the humanized antibody comprises a VH1 acceptor framework and a VK3 acceptor framework. It will be appreciated, however, CDR grafting onto a subset of frameworks does not always result in stable antibodies because there may be some incompatibility between the CDR and the framework residues. This is often compensated for by mutations in the framework region to recover the native mouse structure pair (Honegger et al., *Protein Eng Des Sel,* 22: 121-34 (2009); Kugler et al., *Protein Eng Des Sel,* 22: 135-47 (2009); and Apgar et al., supra). Such framework mutations may be included in the humanized antibody disclosed herein.

An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free $—NH_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the humanized antibody or antigen-binding fragment thereof (e.g., insertion into the heavy and/or light chain variable region amino acid sequence). Any number of any suitable amino acids can be inserted into the amino acid sequence of the humanized antibody or antigen-binding fragment thereof. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the humanized antibody or antigen-binding fragment thereof. For example, 1-10 amino acids (e.g., 1, 2, 3, 4, 5, 6, 7, 8, 9, or 10 amino acids) may be inserted into the amino acid sequence of the humanized antibody or antigen-binding fragment thereof. In this respect, the amino acid(s) can be inserted into the humanized antibody or antigen-binding fragment thereof in any suitable location. Preferably, the amino acid(s) are inserted into a CDR (e.g., CDR1, CDR2, or CDR3) or a framework region of the humanized antibody or antigen-binding fragment thereof.

In some embodiments, the humanized antibody or antigen-binding fragment thereof may comprise one or more modifications to enhance effector functions. It will be appreciated that the antibody constant region (Fc) mediates downstream effector functions via its interaction with Fc-receptors on (innate) immune cells or with the complement system. The interaction with Fc-receptors can lead to killing of cells through a variety of immune effector mechanisms, including antibody-dependent cell-mediated cytotoxicity (ADCC). ADCC refers to the killing of antibody-coated target cells by cells with Fc receptors that recognize the constant region of the bound antibody. Most ADCC is mediated by natural killer (NK) cells that have the Fc receptor FcγRIII or DD16 on their surface. Antibody-mediated complement activation may lead to complement-dependent cytotoxicity (CDC). CDC is the mechanism by which antibody-coated target cells recruit and activate components of the complement cascade, leading to the formation of a Membrane Attack Complex (MAC) on the cell surface and subsequent cell lysis.

Fc receptor-dependent functional activity, such as antibody-dependent cellular cytotoxicity (ADCC), is an important mechanism for the clinical activity of many therapeutic antibodies. In addition, the structure of N-linked glycans linked to a conserved asparagine at amino acid position 297 (N297) of IgG1 heavy chains plays an important role in the conformation and stability of the Fc region (Zheng et al., *MAbs,* 3: 568-76 (2011); and Fang et al., *Biochemistry,* 55: 860-8 (2016)). The absence of the core fucose from the Fc structure results in antibodies with higher binding affinity to FcγRIIIa on macrophages and natural killer (NK) cells, leading to increased ADCC effector function (Scallon et al., *Int Immunopharmacol,* 7: 761-72 (2007); Stavenhagen et al., *Cancer Res,* 67: 8882-90 (2007); Presta et al., *Biochem Soc Trans,* 30: 487-90 (2002); Shinkawa et al., *Biol Chem.,* 278: 3466-73 (2003); Niwa et al., *Cancer Res.,* 64: 2127-33 (2004); Okazaki et al., *J Mol Biol,* 336: 1239-49 (2004); and Shields et al., *J Biol Chem,* 277: 26733-40 (2002)) and improved efficacy in vivo (Junttila et al., *Cancer Res,* 70: 4481-937 (2010); and Gerdes et al., *Clin Cancer Res,* 19:1126-38 (2013)). Thus, in some embodiments, the humanized antibody described herein may be modified to alter the glycosylation pattern of the Fc region. For example, the humanized antibody may be engineered to reduce or remove fucosylation, such that it is "afucosylated."

The inventive humanized antibody or antigen-binding fragment thereof is not limited to a polypeptide comprising the specific amino acid sequences described herein. Indeed, the humanized antibody or antigen-binding fragment thereof can comprise any heavy chain polypeptide or light chain polypeptide that competes with the inventive humanized antibody or antigen-binding fragment thereof for binding to KCNK9. Antibody competition can be assayed using routine peptide competition assays such as, for example, ELISA, Western blot, or immunohistochemistry methods (see, e.g., U.S. Pat. Nos. 4,828,981 and 8,568,992; and Braitbard et al., *Proteome Sci.,* 4: 12 (2006)).

Typically, humanized antibodies are monoclonal. The term "monoclonal antibody," as used herein, refers to an antibody produced by a single clone of B lymphocytes that is directed against a single epitope on an antigen. Monoclonal antibodies typically are produced using hybridoma technology, as first described in Kohler and Milstein, *Eur. J. Immunol.,* 5: 511-519 (1976). Monoclonal antibodies may also be produced using recombinant DNA methods (see, e.g., U.S. Pat. No. 4,816,567), isolated from phage display antibody libraries (see, e.g., Clackson et al. *Nature,* 352: 624-628 (1991)); and Marks et al., *J. Mol. Biol.,* 222: 581-597 (1991)), or produced from transgenic mice carrying a fully human immunoglobulin system (see, e.g., Lonberg, *Nat. Biotechnol.,* 23(9): 1117-25 (2005), and Lonberg, Handb. Exp. Pharmacol., 181: 69-97 (2008)). In contrast, "polyclonal" antibodies are antibodies that are secreted by different B cell lineages within an animal. Polyclonal antibodies are a collection of immunoglobulin molecules that recognize multiple epitopes on the same antigen.

The disclosure further provides a nucleic acid sequence encoding the aforementioned humanized antibody or antigen-binding fragment thereof. In certain embodiments, the nucleic acid sequence is in the form of a vector. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual,* 4th edition, Cold Spring Harbor Press, Cold Spring Harbor, N.Y. (2012), and Ausubel et al., *Current Protocols in Molecular Biology*, Greene Publishing Associates and John Wiley & Sons, New York, N.Y. (1994)).

In addition to the nucleic acid encoding the humanized antibody or antigen-binding fragment thereof, the vector desirably comprises expression control sequences, such as promoters, enhancers, polyadenylation signals, transcription terminators, internal ribosome entry sites (IRES), and the like, that provide for the expression of the antibody-encoding nucleic sequence in a host cell. Exemplary expression control sequences are known in the art and described in, for example, Goeddel, *Gene Expression Technology: Methods in Enzymology*, Vol. 185, Academic Press, San Diego, Calif. (1990).

A vector comprising a nucleic acid sequence encoding the humanized antibody or antigen-binding fragment thereof may be introduced into a host cell that is capable of expressing the polypeptides encoded thereby, including any suitable prokaryotic or eukaryotic cell. Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102). Suitable eukaryotic cells are known in the art and include, for example, yeast cells, insect cells, and mammalian cells. Examples of suitable yeast cells include those from the genera *Hansenula, Kluyveromyces, Pichia, Rhinosporidium, Saccharomyces*, and *Schizosaccharomyces*. Suitable insect cells include Sf-9 and HIS cells (Invitrogen, Carlsbad, Calif.) and are described in, for example, Kitts et al., Biotechniques, 14: 810-817 (1993): Lucklow, *Curr. Opin. Biotechnol.,* 4: 564-572 (1993); and Lucklow et al., *J. Virol.,* 67: 4566-4579 (1993). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA,* 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants also are suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of such cells are well known in the art (see, e.g., Ausubel et al., eds., *Short Protocols in Molecular Biology,* 5th ed., John Wiley & Sons, Inc., Hoboken, N.J. (2002)). Preferably, the mammalian cell is a human cell.

A nucleic acid sequence encoding the heavy or light chains of the humanized antibody may be introduced into a cell by any suitable method, including, for example, by transfection, transformation, or transduction. The terms "transfection," "transformation," and "transduction" are used interchangeably herein and refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol.* 7, Gene Transfer and Expression Protocols, Humana Press (1991)); DEAE-dextran; electroporation; cationic liposome-mediated transfection; tungsten particle-facilitated microparticle bombardment (Johnston, *Nature,* 346: 776-777 (1990)); strontium phosphate DNA co-precipitation (Brash et al., *Mol. Cell. Biol.,* 7: 2031-2034 (1987); and magnetic nanoparticle-based gene delivery (Dobson, J., *Gene Ther,* 13 (4): 283-7 (2006)). Phage or viral vectors can be introduced into host cells, after growth of infectious particles in suitable packaging cells, many of which are commercially available.

Methods of Use

The disclosure also provides methods of using the above-described humanized antibody, or compositions comprising same, to inhibit the activity of KCNK9 in cells (e.g., cancer cells). Thus, the disclosure provides a composition comprising an effective amount of the above-described humanized antibody (or antigen-binding fragment thereof), the nucleic acid sequence encoding the humanized antibody, or the vector comprising the nucleic acid sequence. Preferably, the composition is a pharmaceutically acceptable (e.g., physiologically acceptable) composition, which comprises a carrier, preferably a pharmaceutically acceptable (e.g., physiologically acceptable) carrier, and the humanized antibody, nucleic acid sequence encoding same, or vector described herein. Any suitable carrier can be used within the context of the disclosure, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy,* 21st Edition, Lippincott Williams & Wilkins, Philadelphia, Pa. (2001).

In some embodiments, the disclosure provides a method of inhibiting KCNK9 activity in a cell, which comprises contacting a cell expressing KCNK9 with the above-described humanized antibody (or antigen-binding fragment thereof) or the above-described composition, whereby the humanized antibody binds to KCNK9 expressed by the cell and inhibits KCNK9 activity. The cell may be any suitable cell or cell line that expresses, or is suspected of expressing, KCNK9. The cell desirably expresses KCNK9 at the cell surface.

The phrase "inhibiting KCNK9 activity," as used herein, refers to the ability of the humanized antibody or composition to interfere with the expression and/or biological activity or function of KCNK9. The degree of inhibition may be partially complete (e.g., 10% or more, 25% or more, 50% or more, or 75% or more), substantially complete (e.g., 85% or more, 90% or more, or 95% or more), or fully complete (e.g., 98% or more, or 99% or more). In some embodiments, binding of the humanized antibody or antigen-binding fragment thereof to at least one epitope on the surface of a cell that expresses KCNK9 causes internalization and endocytosis of potassium channels on the surface of the cell.

In some embodiments, binding of the humanized antibody or antigen-binding fragment thereof to at least one epitope on the surface of a KCNK9-expressing cell inhibits the growth and/or survival of the KCNK9-expressing cell, such as a cancer or tumor cell. As such, the disclosure also provides method of inhibiting the growth or survival of a cancer cell comprising contacting a cancer cell with the above-described humanized antibody or composition. The method ideally induces cytotoxicity in tumor cells or cancer cells. The tumor cells or cancer cells may be from a carcinoma (cancer arising from epithelial cells), a sarcoma (cancer arising from bone and soft tissues), a lymphoma (cancer arising from lymphocytes), a blood cancer (e.g., myeloma or leukemia), a melanoma, or brain and spinal cord tumors. The tumor or cancer cells can be located in the oral cavity (e.g., the tongue and tissues of the mouth) and pharynx, the digestive system, the respiratory system, bones and joints (e.g., bony metastases), soft tissue, the skin (e.g., melanoma), breast, the genital system, the urinary system, the eye and orbit, the brain and nervous system (e.g., glioma), or the endocrine system (e.g., thyroid) and are not necessarily from the primary tumor. More particularly, cancers of the digestive system can affect the esophagus, stomach, small intestine, colon, rectum, anus, liver, gall bladder, and pancreas. Cancers of the respiratory system can affect the larynx, lung, and bronchus and include, for example, non-small cell lung carcinoma. Cancers of the reproductive system can affect the uterine cervix, uterine corpus, ovaries, vulva, vagina, prostate, testis, and penis. Cancers of the urinary system can affect the urinary bladder, kidney, renal pelvis, and ureter. Cancer cells also can be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). In some embodiments, the KCNK9-expressing cells comprise breast cancer cells. In some embodiments, the KCNK9-expressing cells comprise lung cancer cells. In some embodiments, the KCNK9-expressing cells are obtained from a subject suffering from small cell lung cancer. In some embodiments, the KCNK9-expressing cells are obtained from a subject suffering from non-small cell lung cancer. The cancer cells may be located in a primary tumor, or alternatively, the cancer cells may be metastatic cancer cells.

Ideally, the disclosed method promotes inhibition of tumor cell proliferation, the eradication of tumor cells, and/or a reduction in the size of at least one tumor such that a mammal (e.g., a human) is treated for cancer. By "treatment of cancer" is meant alleviation of cancer in whole or in part. In one embodiment, the disclosed method reduces the size of a tumor by at least about 20% (e.g., at least about 25%, 30%, 35%, 40%, 45%, 50%, 55%, 60%, 65%, 70%, 75%, 80%, 85%, 90%, or 95%). In some embodiments, the humanized antibody or antigen-binding fragment thereof inhibits survival of at least 10%, at least 20%, at least 30%, at least 40%, at least 50%, at least 60%, at least 70%, or at least 75% of KCNK9-expressing cells in a tumor (e.g., a breast tumor, lung tumor, etc.). In some embodiments, the humanized antibody or antigen-binding fragment thereof inhibits survival of at least 85%, at least 90%, at least 95%, at least 96%, at least 97%, at least 98%, or at least 99% of KCNK9-expressing cells in a bulk tumor (e.g., a breast tumor, lung tumor, etc.). In some embodiments, the humanized antibody or antigen-binding fragment thereof inhibits survival of all KCNK9-expressing cells in a tumor (e.g., a breast tumor, lung tumor, etc.). Ideally, the tumor is completely eliminated.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease (e.g., cancer). To this end, the inventive method comprises administering a "therapeutically effective amount" of the humanized antibody or antigen-binding fragment thereof. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the humanized antibody to elicit a desired response in the individual. For example, a therapeutically effective amount of the humanized antibody of the invention is an amount which decreases KCNK9 protein bioactivity in a human and/or induces cytotoxicity of KCNK9 expressing cells (e.g., CDC or ADCC).

Alternatively, the pharmacologic and/or physiologic effect may be prophylactic, i.e., the effect completely or partially prevents a disease or symptom thereof. In this respect, the inventive method comprises administering a "prophylactically effective amount" of the humanized antibody or antigen-binding fragment thereof. A "prophylactically effective amount" refers to an amount effective, at dosages and for periods of time necessary, to achieve a desired prophylactic result (e.g., prevention of cancer).

A typical dose can be, for example, in the range of 1 pg/kg to 20 mg/kg of animal or human body weight; however, doses below or above this exemplary range are within the scope of the invention. The daily parenteral dose can be about 0.00001 μg/kg to about 20 mg/kg of total body weight (e.g., about 0.001 μg/kg, about 0.1 μg/kg, about 1 μg/kg, about 5 μg/kg, about 10 μg/kg, about 100 μg/kg, about 500 μg/kg, about 1 mg/kg, about 5 mg/kg, about 10 mg/kg, or a range defined by any two of the foregoing values), preferably from about 0.1 μg/kg to about 10 mg/kg of total body weight (e.g., about 0.5 μg/kg, about 1 μg/kg, about 50 μg/kg, about 150 μg/kg, about 300 μg/kg, about 750 μg/kg, about 1.5 mg/kg, about 5 mg/kg, or a range defined by any two of the foregoing values), more preferably from about 1 μg/kg to 5 mg/kg of total body weight (e.g., about 3 μg/kg, about 15 μg/kg, about 75 μg/kg, about 300 μg/kg, about 900 μg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The KCNK9-expressing cells may be contacted with the composition in vitro or in vivo. the term "in vivo" refers to a method that is conducted within living organisms in their normal, intact state, while an "in vitro" method is conducted using components of an organism that have been isolated from its usual biological context. When the cell is contacted with the composition in vitro, the cell may be any suitable prokaryotic or eukaryotic cell. When the cell is contacted with the composition in vivo, the composition may be administered to an animal, such as a mammal, particularly a human, using standard administration techniques and routes. Suitable administration routes include, but are not limited to, oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. In other embodiments, the composition may be administered to a mammal using systemic delivery by intravenous, intramuscular, intraperitoneal, or subcutaneous injection.

The disclosed method can be performed in combination with other therapeutic methods to achieve a desired biological effect in a patient. Ideally, the disclosed method may include, or be performed in conjunction with, one or more cancer treatments. The choice of cancer treatment used in combination with the disclosed method will depend on a variety of factors, including the cancer/tumor type, stage and/or grade of the tumor or cancer, the patient's age, etc. Suitable cancer treatments that may be employed include, but are not limited to, surgery, chemotherapy, radiation therapy, immunotherapy, hormone therapy, and stem cell transplantation. In one embodiment, the disclosed method further comprises treating the cancer cells with a chemotherapeutic agent. Any suitable chemotherapeutic agent can be used in the disclosed method, including, for example, adriamycin, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, floxuridine, fludarabine, fluorouracil, gemcitabine, hydroxyurea, idarubicin, ifosfamide, irinotecan, lomustine, mechlorethamine, mercaptopurine, meplhalan, methotrexate, mitomycin, mitotane, mitoxantrone, nitrosurea, paclitaxel, pamidronate, pentostatin, plicamycin, procarbazine, rituximab, streptozocin, teniposide, thioguanine, thiotepa, vinblastine, vincristine, vinorelbine, taxol, transplatinum, anti-vascular endothelial growth factor compounds ("anti-VEGFs"), anti-epidermal growth factor receptor compounds ("anti-EGFRs"), 5-fluorouracil, and the like. The type and number of chemotherapeutics used in the disclosed method will depend on the standard chemotherapeutic regimen for a particular tumor type.

Kits

The humanized antibody or antigen-binding fragment thereof can be provided in a kit, i.e., a packaged combination of reagents in predetermined amounts with instructions for using the antibody (e.g., for administration to a human subject). As such, the disclosure provides a kit comprising the humanized antibody or antigen-binding fragment described herein and instructions for use thereof. The instructions can be in paper form or computer-readable form, such as a disk, CD, DVD, etc. Ideally, the kit comprises all components, i.e., reagents, standards, buffers, diluents, etc., which are necessary to deliver the composition to cells in vitro or in vivo. The kit components may be provided as dry powders (typically lyophilized), including excipients which on dissolution will provide a reagent solution having the appropriate concentration.

The following examples further illustrate the invention but, of course, should not be construed as in any way limiting its scope.

Example 1

This example describes the construction and expression of a humanized version of a KCNK9-specific mouse monoclonal antibody.

An anti-KCNK9 mouse monoclonal antibody having a $V_H$ amino acid sequence of SEQ ID NO: 1 and a $V_L$ amino acid sequence of SEQ ID NO: 2 (mu-mAb) was humanized using a method based on Queen et al., *Proc. Natl. Acad. Sci. USA,* 86: 10029-10033 (1989). The hybridoma antibody was sequenced after amplifying the antibody variable regions by RT-PCR with degenerate primers. The variable regions were fused with the human antibody IgG1 constant regions to produce a chimeric antibody. Antigen binding of the chimeric antibody was confirmed by staining of the KCNK9-expressing cells. HEK293 cells were stably transfected with KCNK9 expression vector under the tetracycline inducible promoter. After induction, the cells were incubated with various concentrations of chimeric KCNK9 antibody for 30 minutes, followed by secondary anti-human Fc FITC conjugate. Chimeric antibody binding was analyzed by flow cytometry. High affinity binding was confirmed with an $EC_{50}$ of about 0.3 μg/mL (FIG. 1A).

Figure 1B:
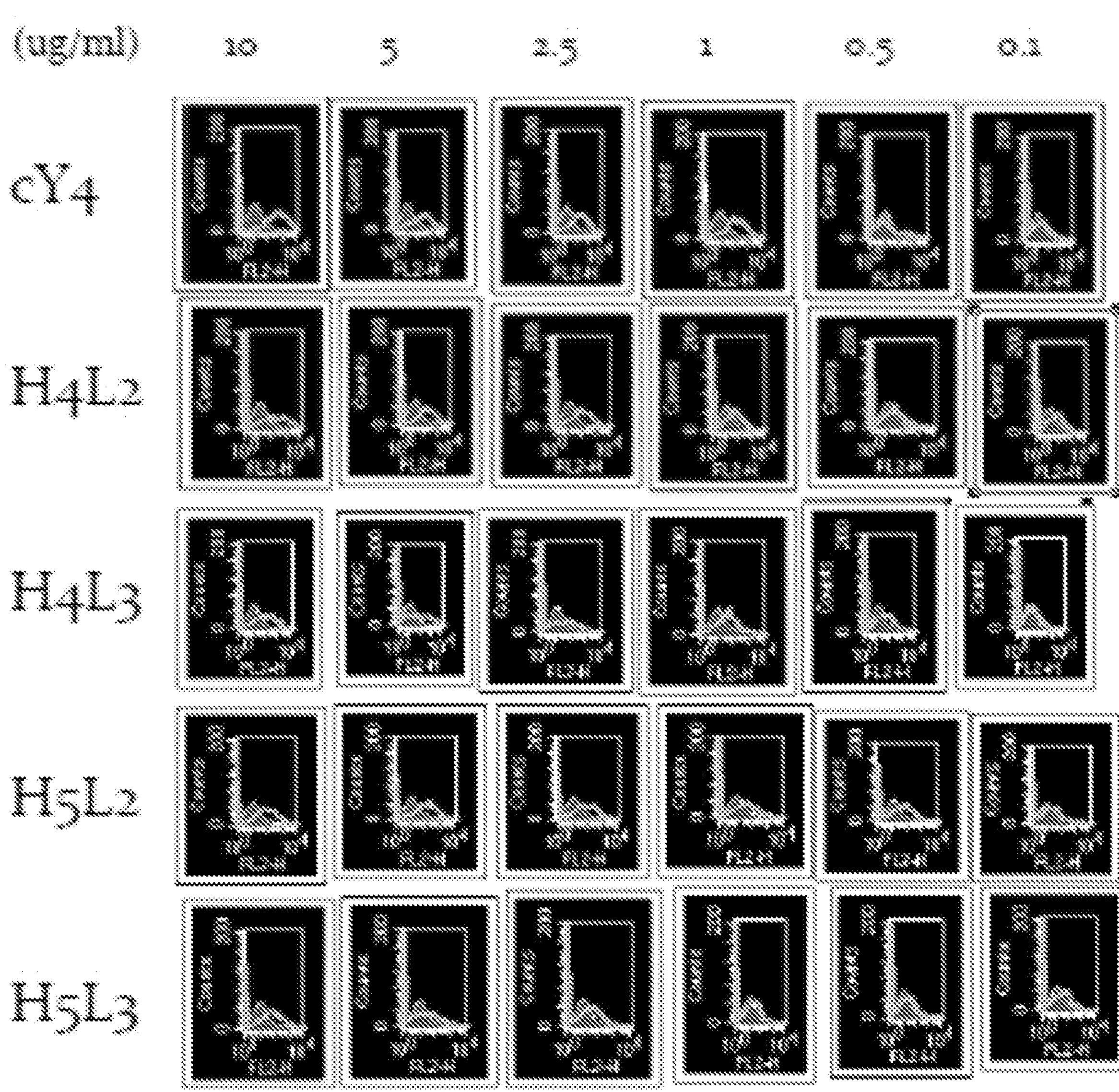
FIG. 1B includes images of chimeric and humanized KCNK9 monoclonal antibodies stained with anti-human Fc PE secondary antibody.

After antibody sequence analysis and structure modeling, the murine antibody CDRs (SEQ ID NOs: 3-8) were grafted into human antibody VK3-11 and VH1-3 frameworks. Critical murine antibody framework residues that support CDR conformation were identified and introduced into the human frameworks. Five variants of the humanized VH sequences (VH1-5; SEQ ID NOs: 9-13) and three variants of the humanized VL variants (VL1-3; SEQ ID NOs: 14-16) were designed and synthesized. All of the variable regions were cloned into a human IgG1 expression vector. The VHs and VLs were cross-matched to generate 15 humanized KCNK9 antibody clones. All humanized antibodies were produced by transient transfection in 293 cells and purified by Protein A chromatography. Antigen binding of the humanized KCNK9 antibodies was characterized by immunofluorescence staining of KCNK9-expressing cells. Nine of 15 clones exhibited positive binding at 1 μg/mL (FIG. 1A). After switching to a PE conjugate secondary antibody with more intense fluorescence signal, clones H4L3 (SEQ ID NO: 12 and SEQ ID NO: 16, respectively) and H5L2 (SEQ ID NO: 13 and SEQ ID NO: 15, respectively) were found to be the best humanized variants and demonstrated binding to human KCNK9 with a higher affinity than their parental KCNK9 murine monoclonal antibody (FIG. 1B).

Example 2

This example describes the binding, specificity, and in vitro functional activity of wild-type and afucosyl humanized KCNK9 monoclonal antibodies.

The antibody-dependent cellular cytotoxicity (ADCC) and complement-dependent cytotoxicity (CDC) of lead humanized monoclonal antibody clones H4L3 and H5L2 were evaluated. Since the fucose of the N-glycan on the antibody Fc region is known to interfere with the interaction between the antibody and the FcγIII receptor and therefore inhibit ADCC, afucosyl versions of H4L3 and H5L2 antibodies (AF-H4L3 and AF-H5L2) were generated using proprietary fut$8^{-/-}$ CHO cells. The ADCC activities of the non-modified H4L3 and H5L2 antibody clones were compared to the afucosyl variants thereof.

Figure 2:
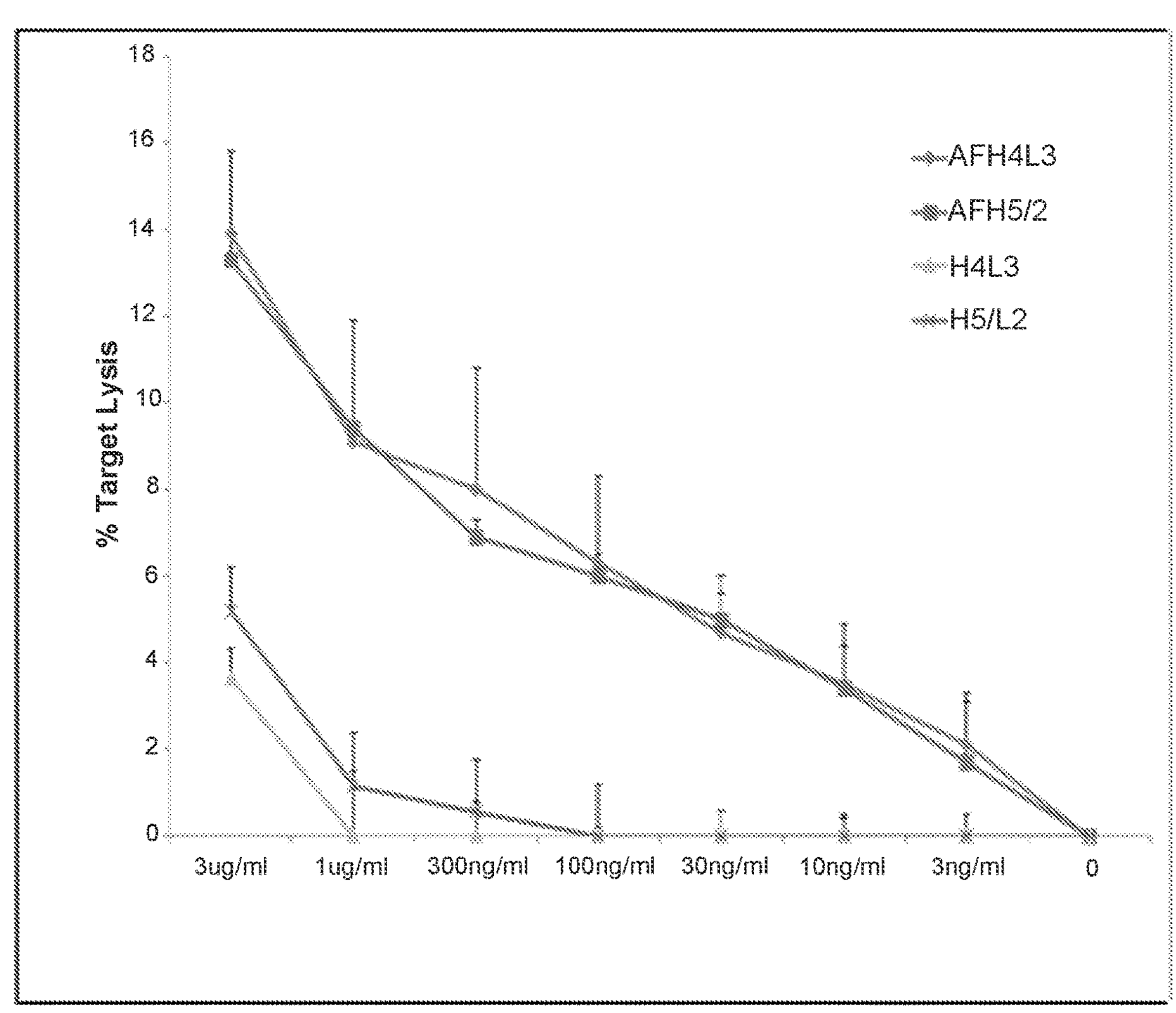
FIG. 2 is a graph showing the ADCC activities of wild type and afucosyl humanized antibodies using KCNK9-expressing HEK293 target cells and NK effector cells as described in Example 2.

KCNK9-expressing HEK293 cells were used as the target cells and proprietary NK92 cells stably expressing human FcγIII (NK92-3F9) were used as effector cells. After KCNK9 expression in HEK293 cells was induced for 48 hours, cells were plated at 1000 cells/well in 96-well plates overnight in RPMI with 2% FBS. The NK94-3F9 cells were added to the plates at a 10:1 ratio in the presence of various antibodies. Cell lysis was assessed by a cytotoxicity assay (Promega Corp, Madison, Wis.) after six hours. The non-modified antibodies exhibited little ADCC activity, whereas the afucosyl variants exhibited 100-fold enhancement of ADCC activity (FIG. 2). The CDC activity of the humanized monoclonal antibodies also was tested. The KCNK9-expressing HEK293 cells were mixed with human serum and various concentrations of the non-modified and afucosyl monoclonal antibodies. None of these antibodies exhibited any CDC activity, suggesting that CDC is not a potential functional mechanism of the humanized antibodies.

Figure 3:
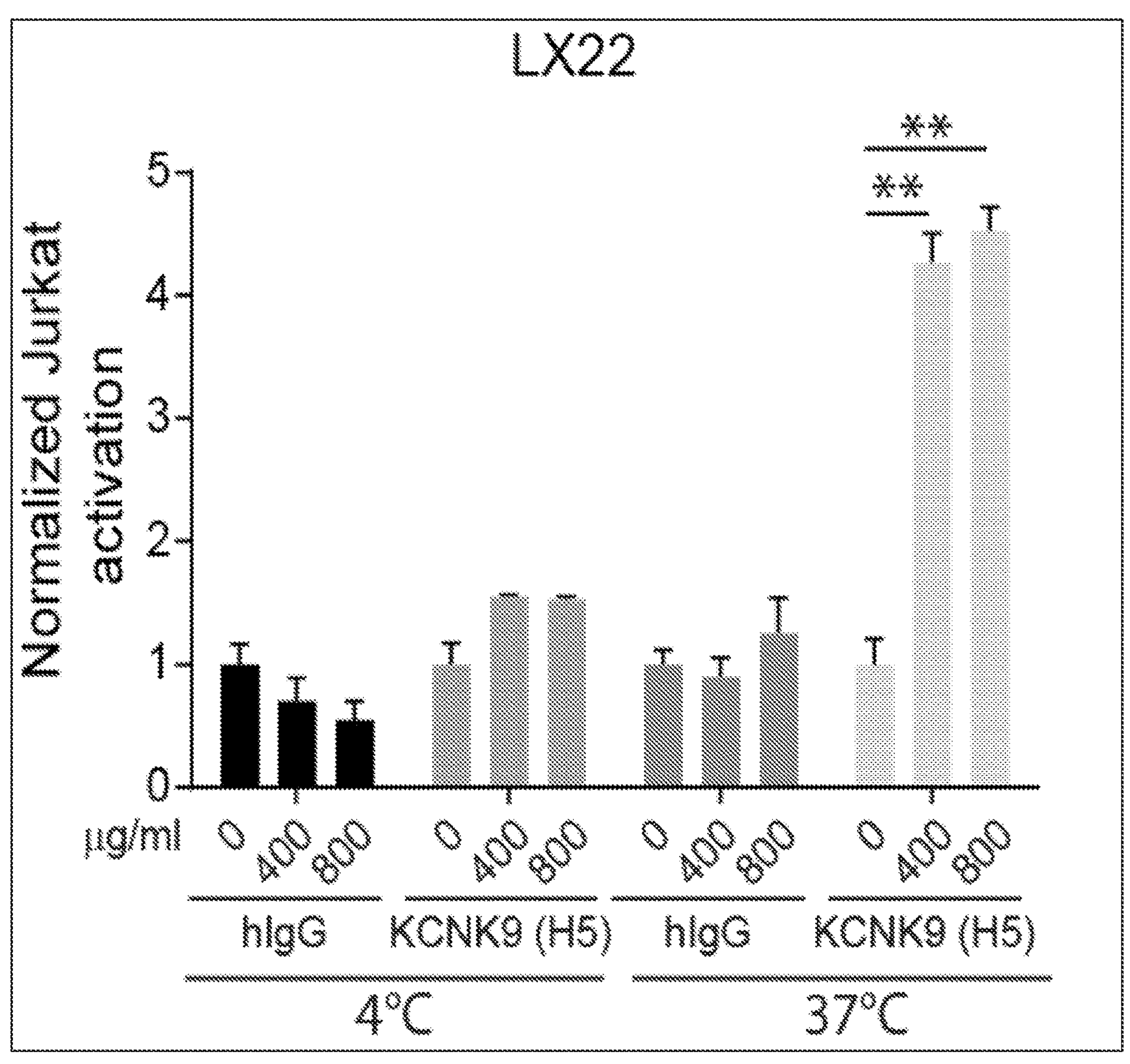
FIG. 3 is a graph showing ADCC activity induced by the AF-H5L2 (AF-H5) KCNK9 monoclonal antibody using patient-derived LX22 small cell lung cancer target cells and a luciferase Jurkat effector cell assay as described in Example 2. Luciferase activity normalized to IgG1 is shown (**$p<0.01$).

The capacity of the humanized KCNK9 AF-H5L2 monoclonal antibody to induce ADCC directed against LX22 PDX small cell lung cancer cells also was evaluated. ADCC assays were performed using the ADCC Reporter Bioassay Complete Kit (Promega #G7015). Human lung CA KCNK9+LX22 cells or CD20+ Raji cells (as positive control) were plated at 50,000 cells per well. On the following day, humanized afucosyl anti-KCNK9 (hu-AF-H5), hu-anti-CD20, or non-immune huIgG1 (as negative control) was added. 30 minutes later, FcγIIIa+ Jurkat effector cells expressing the vNFAT-luciferase ADCC reporter were added (300,000 cells/well). Cell mixtures were incubated for six hours at either 4° C. or 37° C. Cells were collected, solubilized, and luciferase activity was quantified as a biomarker of Jurkat cell activation. AF-H5L2 induced ADCC that was temperature dependent, as shown in FIG. 3.

Figure 4A:
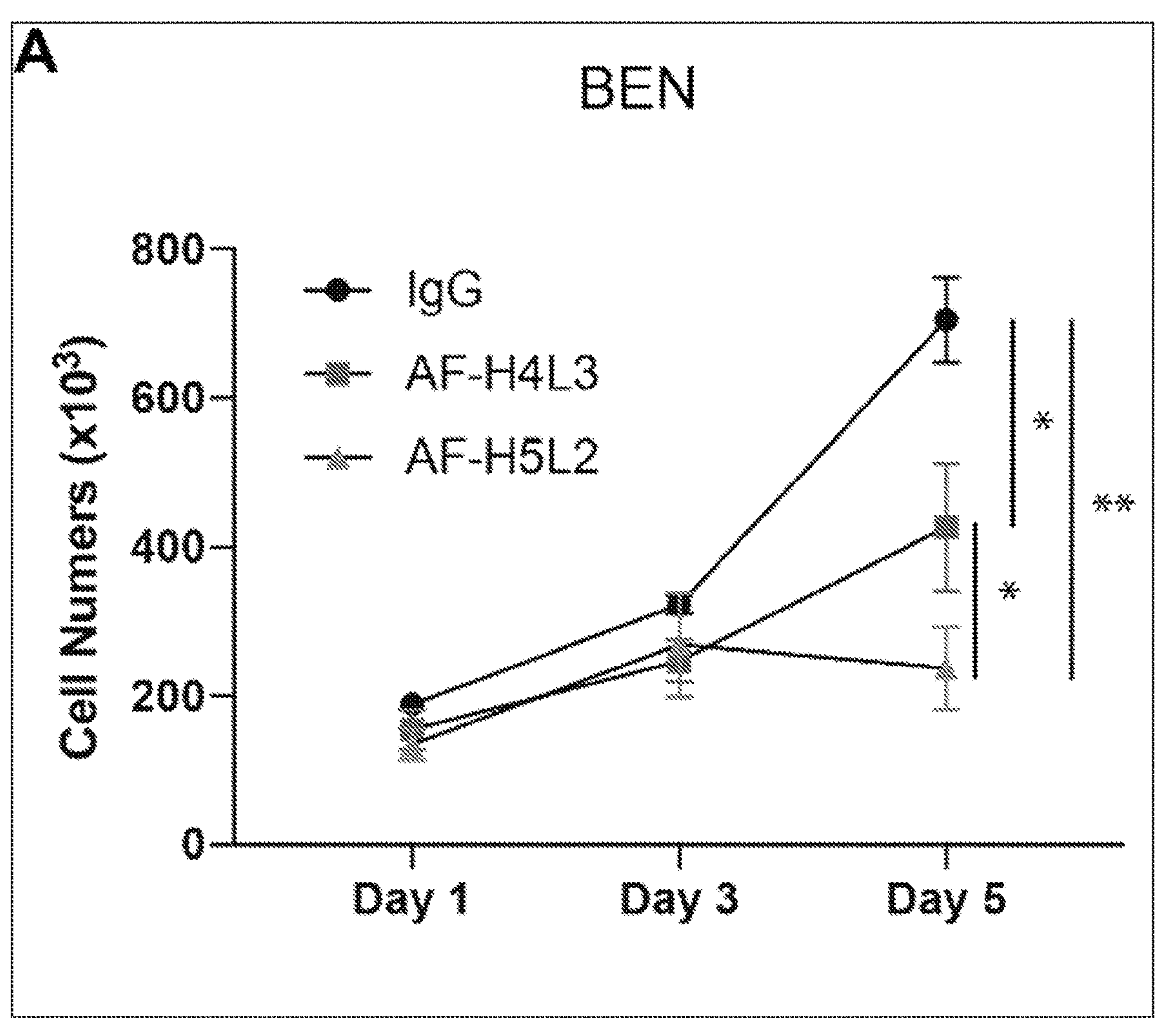
FIGS. 4A-4C illustrate the effects of KCNK9 Abs AF-H4L3 (H4) and AF-H5L2 (H5), or hIgG (negative control) on growth and viability of KCNK9-positive BEN lung carcinoma cells assayed by cell numbers (FIG. 4A), MTT (FIG. 4B), or trypan blue exclusion (FIG. 4C).
Figure 4B:
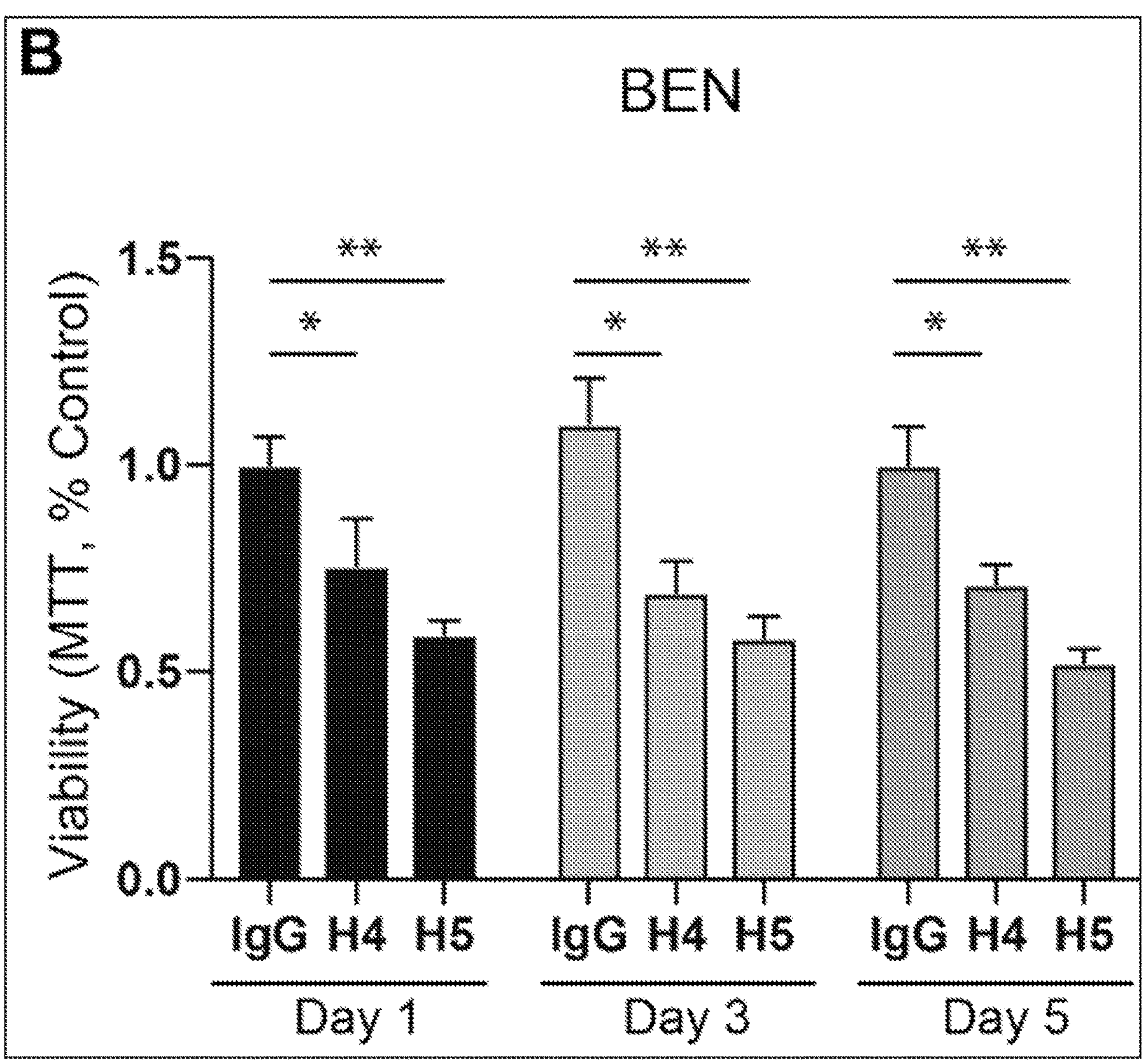
Figure 4C:
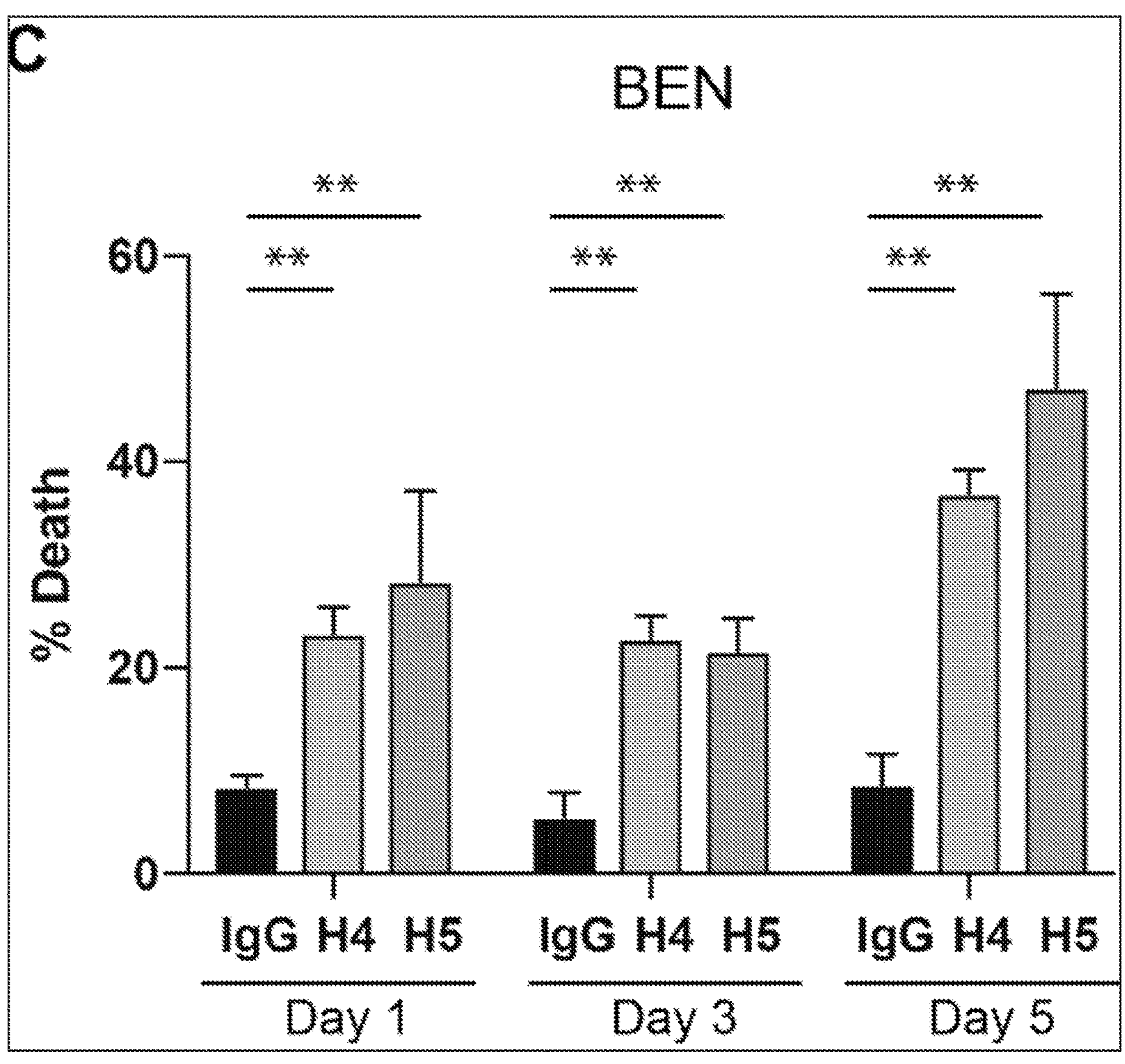
Figure 5:
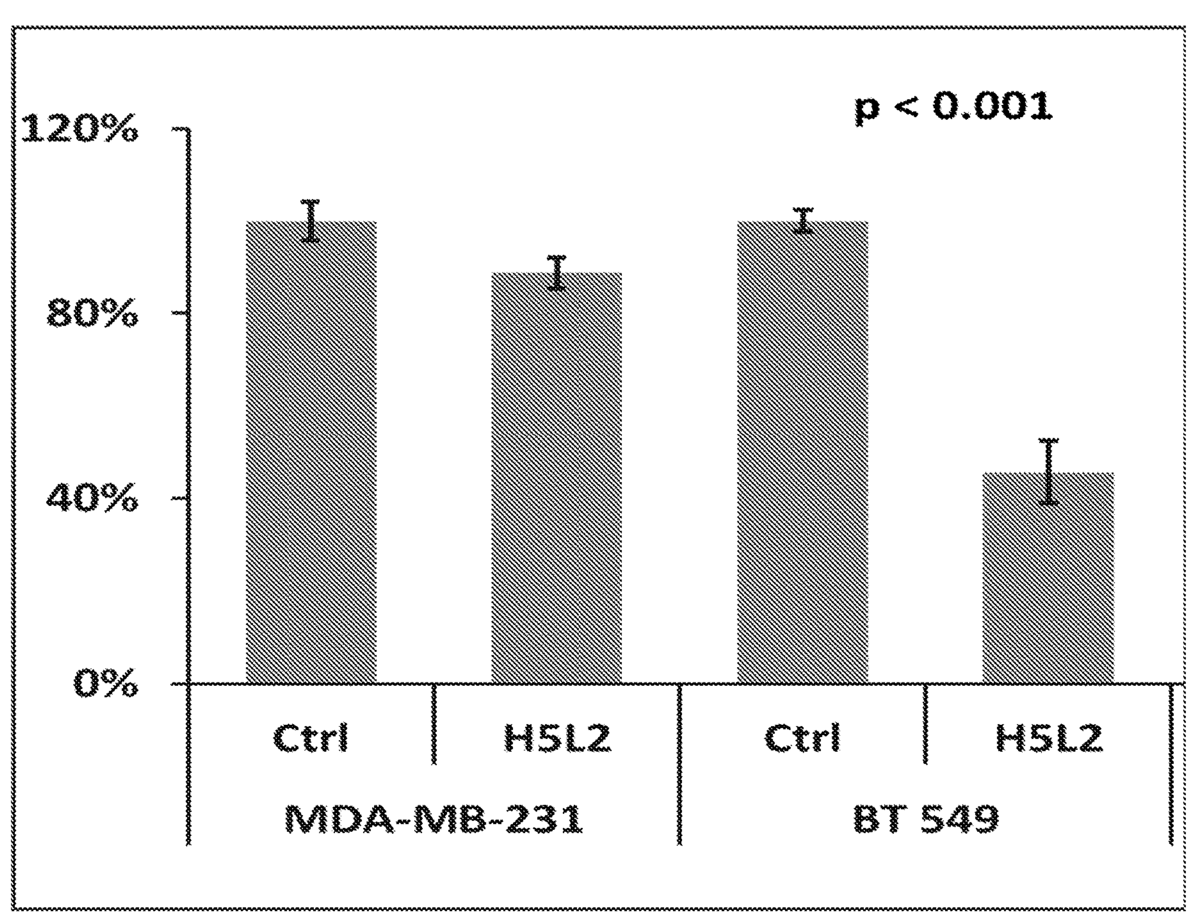
FIG. 5 are graphs showing that AF-H5L2 inhibits the viability of KCNK9-positive BT-549 breast cancer cells and not KCNK9-negative MDA-MB-231 cells.

The cytotoxic effect of the AF-H4L3 and AF-H5L2 monoclonal antibodies was tested on KCNK9-expressing BEN lung carcinoma cells. Equal numbers of viable BEN cells were treated with AF-H4L3, AF-H5L2, or human IgG control (0.4 mg/mL). Cells were collected at indicated days after treatment for cell growth and viability assays. Both humanized monoclonal antibody clones inhibited cell growth and viability, but the AF-H5L2 antibody was comparatively more active (FIGS. 4A-4C). The AF-H5L2 monoclonal antibody similarly inhibited the viability of KCNK9-positive BT549 carcinoma cells without effecting the viability of KCNK9-negative MDA-MB-231 cells (FIG. 5).

Example 3

This example evaluates the functional activity of anti-KCNK9 humanized monoclonal antibodies in human tumor xenograft models in mice.

Figure 6A:
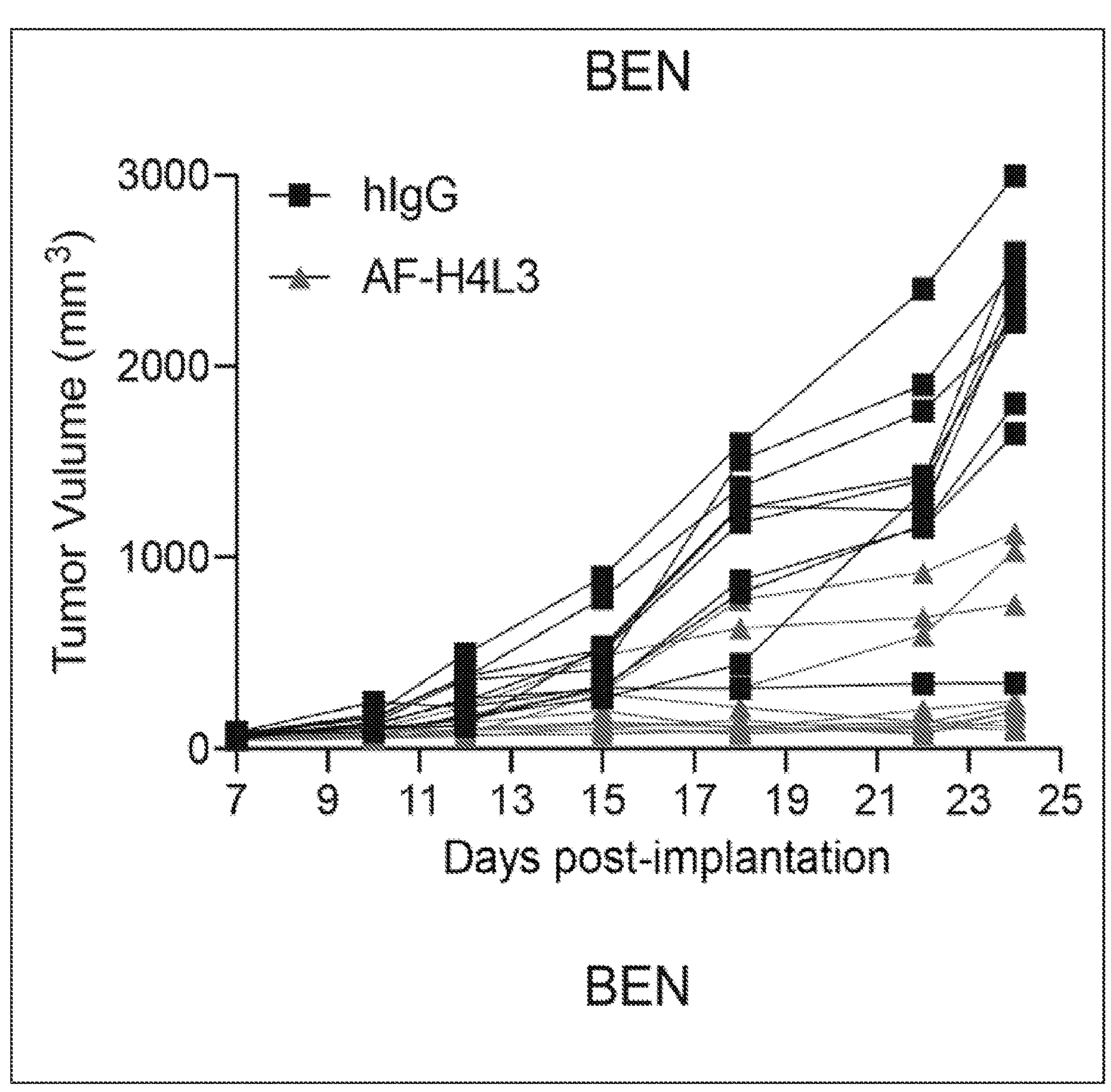
FIGS. 6A and 6B are graphs illustrating that AF-H4L3 and AF-H5L2, respectively, inhibit pre-established BEN lung carcinoma xenografts in mice, shown as growth of individual tumors.
Figure 6B:
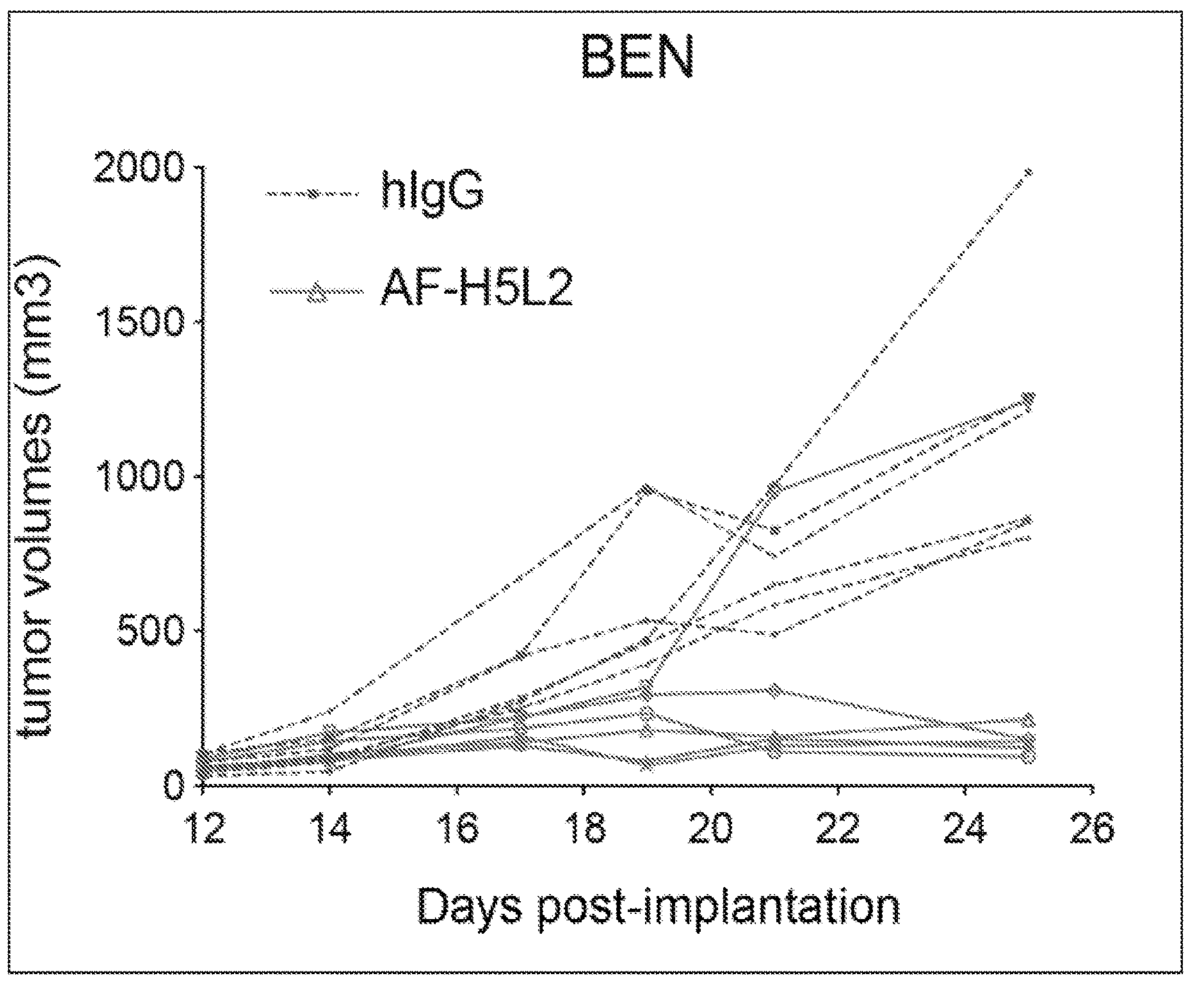
Figure 6C:
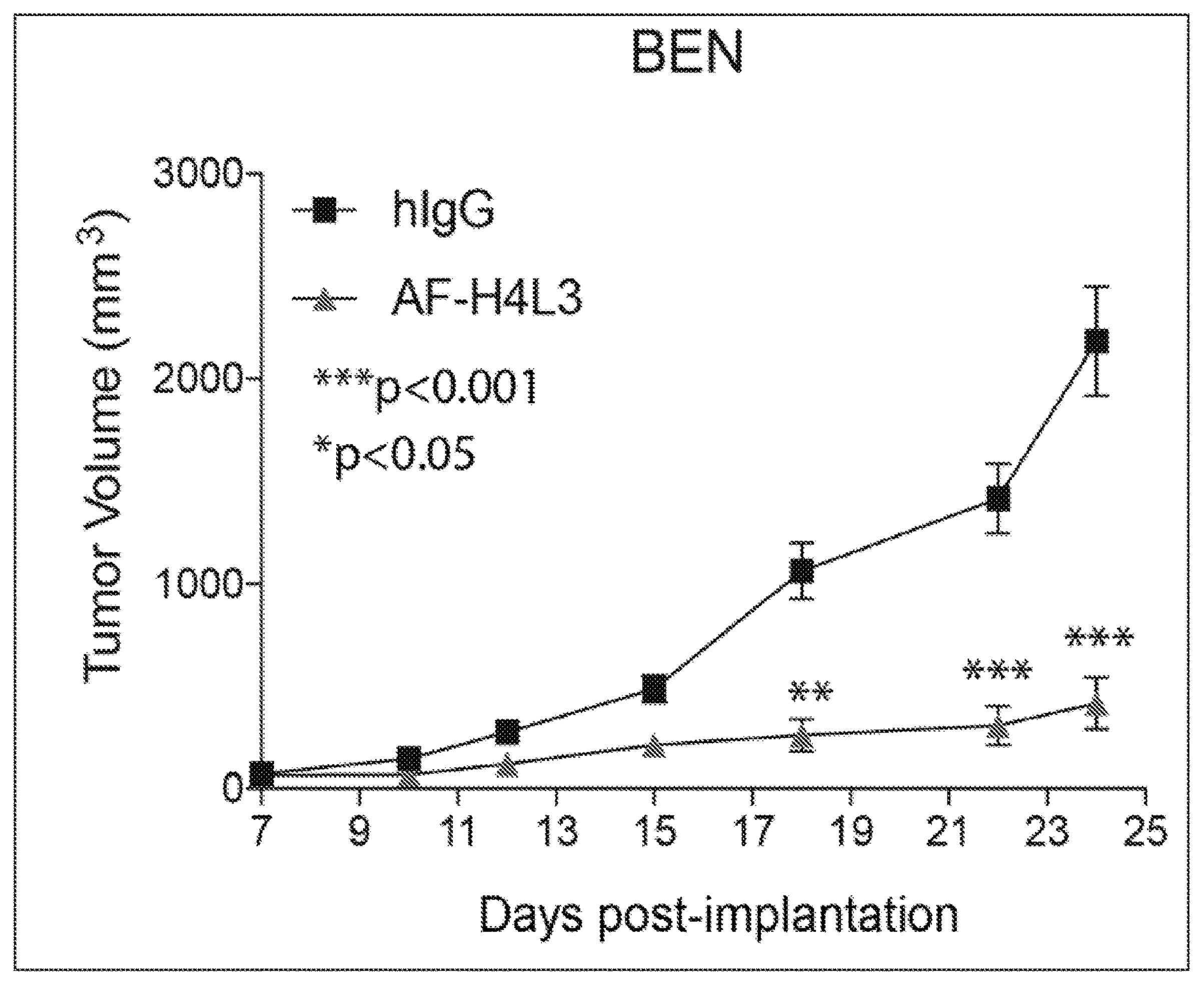
FIGS. 6C and 6D are graphs illustrating that AF-H4L3 and AF-H5L2, respectively, inhibit pre-established BEN lung carcinoma xenografts in mice, shown as mean tumor volumes+/−SEM
Figure 6D:
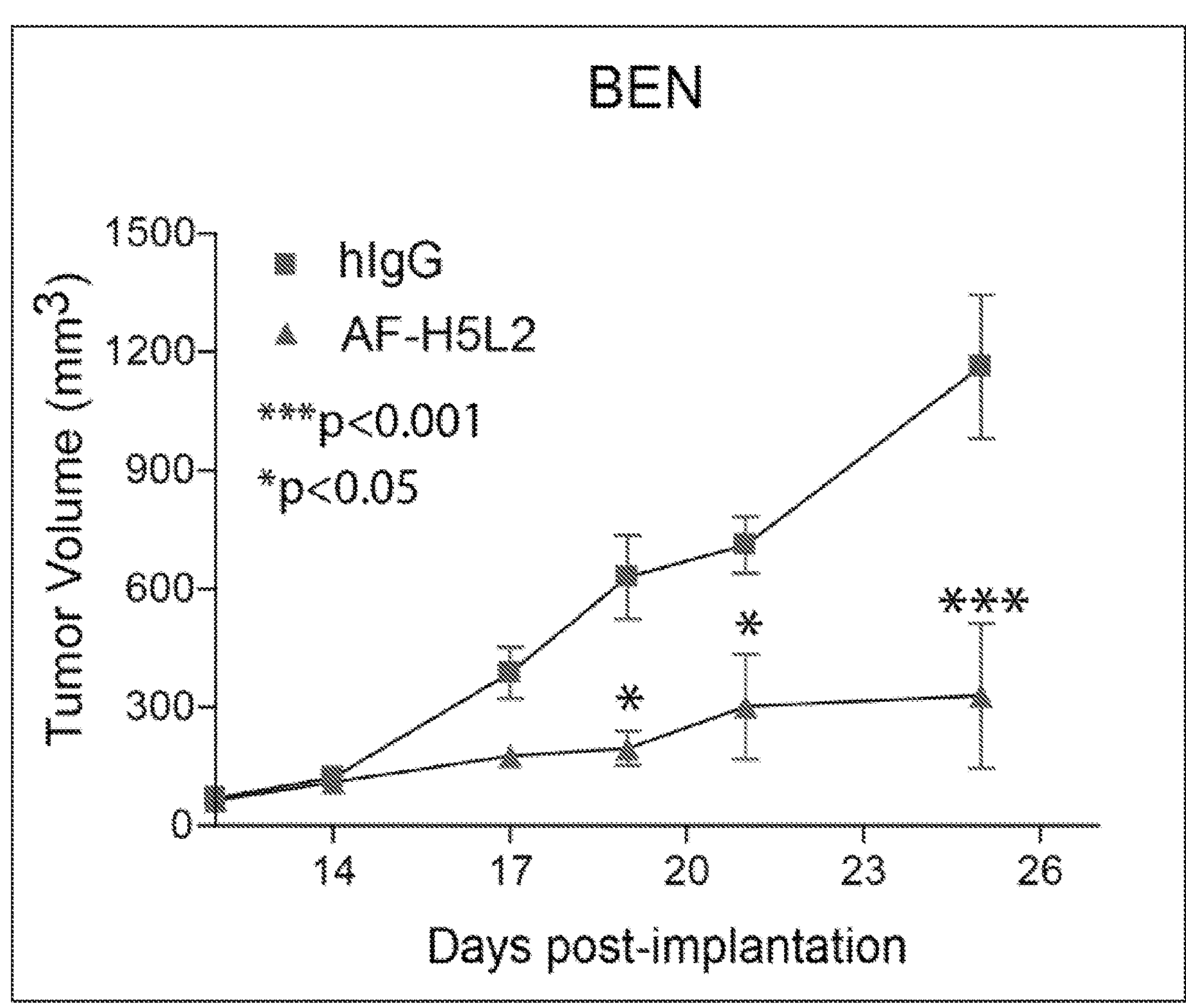

Equal numbers of viable BEN cells ($4\times10^6$ cells) were implanted into the flanks of nude mice. Humanized anti-KCNK9 monoclonal antibodies AF-H4L3, AF-H5L2, or control human IgG (4 mg/kg b.w.) were administered twice per week after tumor xenografts were established and palpable. Tumor volumes were then monitored during treatments using caliper measurements every alternate day (N=10 for each group). Both AF-H4L3 and AF-H5L2 significantly attenuated tumor growth (*p<0.01), as shown in FIGS. 6A-6**D.

Example 4

This example demonstrates that humanized KCNK9 monoclonal antibody AF-H5L2 enhances tumor cell responses to PARP and CDK4/6 inhibition.

Inhibitors of poly-ADP ribose polymerase (PARP) and cyclin dependent kinases (CDK4/6) are FDA-approved and undergoing clinical testing for multiple solid tumors. It was investigated whether inhibiting the KCNK9 $K^+$ channel with huKCNK9 mAb sensitized cancer cells to these therapeutics. Human LX22 PDX-derived lung carcinoma cells were treated with the PARP inhibitor AZD2461 (100 μM)+/− huKCNK9 mAb (400 μg/ml) or with the CDK4/6 inhibitor palbociclib (0.5 μM)+/−huKCNK9 mAb (400 μg/ml) for 72 hours. Cell viability was then quantified by MTT assay. Statistical comparisons were performed by ANOVA and post-hoc Tukey test.

Figure 7A:
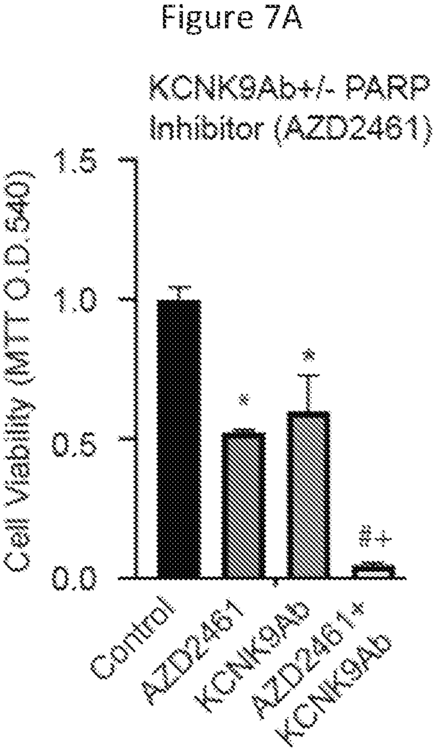
FIGS. 7A and 7B are graphs showing that humanized KCNK9 monoclonal antibody AF-H5L2 enhances tumor cell responses to PARP (7A) and CDK4/6 (7B) inhibition.
Figure 7B:
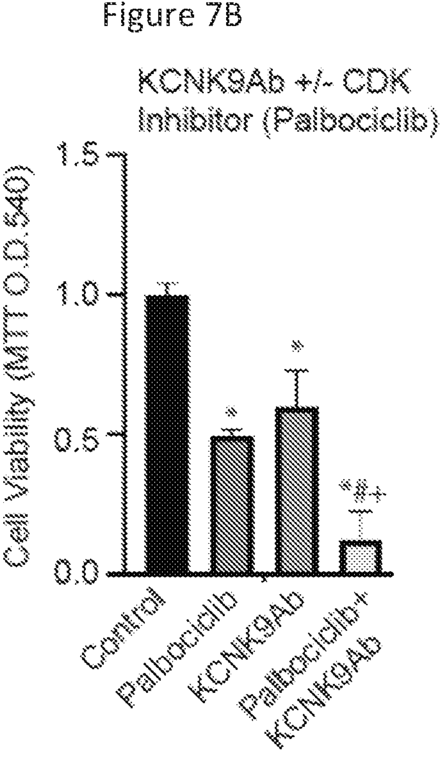

FIGS. 7A and 7B show that lung cancer cell toxicity induced by either PARP inhibition or CDK4/6 inhibition is substantially augmented by treating cells with the huKCNK9 mAb. These results establish in vitro proof-of-concept for combining huKCNK9 mAb with current FDA-approved and emerging cancer therapeutics.

REFERENCES

All references, including publications, patent applications, and patents, cited herein are hereby incorporated by reference to the same extent as if each reference were individually and specifically indicated to be incorporated by reference and were set forth in its entirety herein.

1. Abramovits W, Arrazola P, Gupta A K. 2004. Enbrel (etanercept). Skinmed 3: 333-5.
2. Arcangeli A, Becchetti A. 2015. Novel perspectives in cancer therapy: Targeting ion channels. Drug Resist Updat. 2015 Jul. 6. pii: S1368-7646(15)00034-5. doi: 10.1016/j.drup.2015.06.002.
3. Arcangeli A. 2011. Ion channels and transporters in cancer. 3. Ion channels in the tumor cell-microenvironment cross talk. Am J Physiol Cell Physiol 301: C762-71.
4. Arnould L, Gelly M, Penault-Llorca F, Benoit L, Bonnetain F, Migeon C, Cabaret V, Fermeaux V, Bertheau P, Gamier J, Jeannin J F, Coudert B. 2006. Trastuzumab-based treatment of HER2-positive breast cancer: an antibody-dependent cellular cytotoxicity mechanism? Br J Cancer 94: 259-267.
5. Barel O, Shalev S A, Ofir R, Cohen A, Zlotogora J, Shorer Z, Mazor G, Finer G, Khateeb S, Zilberberg N, Birk O S. 2008. Maternally inherited Birk Barel mental retardation dysmorphism syndrome caused by a mutation in the genomically imprinted potassium channel KCNK9. Am J Hum Genet 83: 193-9.
6. Becchetti A. 2011. Ion channels and transporters in cancer. 1. Ion channels and cell proliferation in cancer. Am J Physiol Cell Physiol 301: C255-65.
7. Becker, C. et al. Protection from graft-versus-host disease by HIV-1 envelope protein gp120-mediated activation of human CD4+CD25+ regulatory T cells. Blood 114, 1263-1269, doi:10.1182/blood-2009-02-206730 (2009).
8. Bhattacharyya S, Bhattacharya R, Curley S, McNiven M A, Mukherjee P. 2010. Nanoconjugation modulates the trafficking and mechanism of antibody induced receptor endocytosis. Proc Natl Acad Sci USA 107:14541-14546.
9. Bittner S, Budde T, Wiendl H, Meuth S G. 2010. From the background to the spotlight: TASK channels in pathological conditions. Brain Pathol 20: 999-1009.
10. Butler A, Hoffman P, Smibert P, Papalexi E, Satija R 2018. Integrating single-cell transcriptomic data across different conditions, technologies, and species. Nat Biotechnol 36: 411-420.
11. Cheng H, Wang S, Feng R. 2016. STIM1 plays an important role in TGF-β-induced suppression of breast cancer cell proliferation. Oncotarget 7: 16866-78.
12. Chou T C, Talalay P. 1984. Quantitative analysis of dose-effect relationships: the combined effects of multiple drugs or enzyme inhibitors. Adv Enzyme Regul. 22:27-55.
13. Coburn C A, Luo Y, Cui M, Wang J, Soll R, Dong J, Hu B, Lyon M A, Santarelli P, Kraus R L, Gregan Y, Wang Y, Fox S V, Binns J, Doran S M, Reiss D R, Tannenbaum P L, Gotter A L, Aleinke P T, Renger J J. 2012. *Discovery of a pharmacologically active antagonist of the two-pore-domain potassium channel K2P9.1 (TASK-3). Chem Med Chem* 7: 123-33.
14. Comes N, Serrano-Albarras A, Capera J, Serrano-Novillo C, Condom E, Ramón Y Cajal S, Ferreres J C, Felipe A. 2015. Involvement of potassium channels in the progression of cancer to a more malignant phenotype. Biochim Biophys Acta. 2014 Dec. 14. pii: S0005-2736) 00436-2. doi: 10.1016/j.bbamem.2014.12.008.
15. Cross B M, Hack A, Timothy A. Reinhardt T A, Rao R. 2013. SPCA2 Regulates Orail Trafficking and Store Independent Ca2+ Entry in a Model of Lactation. PLos One 8:e67348doi:/10.1371/journal.pone.0067348.
16. D'Amico M, Gasparoli L, Arcangeli A. 2013. Potassium channels: novel emerging biomarkers and targets for therapy in cancer. Recent Pat Anticancer Drug Discov 8: 53-65.
17. Dookeran K A, Zhang W, Stayner L, Argos M. 2017. Associations of two-pore domain potassium channels and triple negative breast cancer subtype in The Cancer Genome Atlas: systematic evaluation of gene expression and methylation. BMC Res Notes 10:475. doi: 10.1186/s13104-017-2777-4.
18. Felipe A, Vicente R, Villalonga N, Roura-Ferrer M, Martinez-Mirmol R, Solé L, Ferreres J C, Condom E. 2006. Potassium channels: new targets in cancer therapy. Cancer Detect Prev 30: 375-85.
19. Feng M Y, Rao R. 2013. New insights into store-independent Ca(2+) entry: secretory pathway. Int J Oral Sci. 2013 June; 5(2):71-4. doi: 10.1038/ijos.2013.23. Epub 2013 May 10. Review.
20. Haghverdi L, Buttner M, Wolf F A, Buettner F, Theis F J. 2018. Diffusion pseudotime robustly reconstructs lineage branching. Nat Methods 13: 845-8.
21. Hahn, S. A., Bellinghausen, I., Trinschek, B. & Becker, C. Translating Treg Therapy in Humanized Mice. Frontiers in immunology 6, 623, doi:10.3389/fimmu.2015.00623 (2015).
22. Heinrichs, J. et al. 2016. Regulatory T-Cell Therapy for Graft-versus-host Disease. Journal of immunology research and therapy 1, 1-1.
23. Hsu, Y F, Ajona D, Corrales L, Lopez-Picazo J M, Gurpide A. Montuenga L M, Pio R. 2010. Complement activation mediates cetuximab inhibition of nonsmall cell lung cancer tumor growth in vivo. Molecular Cancer 9:139.

24. Innamaa A, Jackson L, Asher V, Van Shalkwyk G, Warren A, Hay D, Bali A, Sowter H, Khan R. 2013. Expression and prognostic significance of the oncogenic K2P potassium channel KCNK9 (TASK-3) in ovarian carcinoma. Anticancer Res 33: 1401-8.
25. Jemal A, Bray F, Center M M, Ferlay J, Ward E, Forman D. 2011. Global cancer statistics. CA Cancer J Clin 61: 69-90.
26. Kapoor S. 2008. TASK3 and its role in neuro and systemic oncogenesis. J Neurooncol 88: 243.
27. Konishi E, Kitai Y, Kondo T. 2008. Utilization of Complement-Dependent Cytotoxicity To Measure Low Levels of Antibodies: Application to Nonstructural Protein 1 in a Model of Japanese Encephalitis Virus. Clin Vaccine Immunol: CVI 15: 88-94.
28. Kosztka L, Rusznik Z, Nagy D, Nagy Z, Fodor J, Szucs G, Telek A, Gonczi M, Ruzsnavszky O, Szentandrassy N, Csernoch L. 2011. Inhibition of TASK-3 (KCNK9) channel biosynthesis changes cell morphology and decreases both DNA content and mitochondrial function of melanoma cells maintained in cell culture. Melanoma Res 21:308-322.
29. Lehen'kyi V, Shapovalov G, Skryma R, Prevarskaya N. 2011. Ion channels and transporters in cancer. 5. Ion channels in control of cancer and cell apoptosis. Am J Physiol Cell Physiol 301: C1281-9.
30. Litan A, Langhans S A. 2015. Cancer as a channelopathy: ion channels and pumps in tumor development and progression. Front Cell Neurosci 9:86.
31. Lu F, Sun J, Sun T, Cheng H, Yang S. 2018. Fluorescence-Based Measurements of Store-Operated Ca2+ Entry in Cancer Cells Using Fluo-4 and Confocal Live-Cell Imaging. Methods Mol Biol. 1843:63-68. doi: 10.1007/978-1-4939-8704-7.
32. Machaca K. 2010. Ca2+ signaling, genes and the cell cycle. Cell Calcium 48:243-250.
33. Medhurst A D, Rennie G, Chapman C G, Meadows H, Duckworth M D, Kelsell R E, Gloger I I, Pangalos M N. 2001. Distribution analysis of human two pore domain potassium channels in tissues of the central nervous system and periphery. Brain Res Mol Brain Res 86: 101-14.
34. Mendelsohn J. 1997. Epidermal growth factor receptor inhibition by a monoclonal antibody as anticancer therapy. Clin Cancer Res 3: 2703-2707.
35. Meuth S G, Herrmann A M, Ip C W, Kanyshkova T, Bittner S, Weishaupt A. Budde T, Wiendl H. 2008. The two-pore domain potassium channel TASK3 functionally impacts glioma cell death. J Neurooncol 87: 263-70.
36. Molina M A, Codony-Servat J, Albanell J, Rojo F, Arribas J, Baselga J. 2001. Trastuzumab (Herceptin), a Humanized Anti-HER2 Receptor Monoclonal Antibody, Inhibits Basal and Activated HER2 Ectodomain Cleavage in Breast Cancer Cells. Cancer Res 61: 4744-4749.
37. Mu D, Chen L, Zhang X, See L H, Koch C M, Yen C, Tong J J, Spiegel L, Nguyen K C, Servoss A, Peng Y, Pei L, Marks J R, Lowe S, Hoey T, Jan L Y, McCombie W R, Wigler M H, Powers S. 2003. Genomic amplification and oncogenic properties of the KCNK9 potassium channel gene. Cancer Cell 3: 297-302.
38. Mulkey D K, Talley E M, Stornetta R L, Siegel A R, West G H, Chen X, Sen N, Mistry A M, Guyenet P G, Bayliss D A. 2007. TASK channels determine pH sensitivity in select respiratory neurons but do not contribute to central respiratory chemosensitivity. J Neurosci 27; 14049-58.
39. Mutis, T. et al. 2006. Human regulatory T cells control xenogeneic graft-versus-host disease induced by autologous T cells in RAG2−/−gammac−/− immunodeficient mice. Clinical cancer research: an official journal of the American Association for Cancer Research 12, 5520-5525, doi:10.1158/1078-0432.CCR-06-0035.
40. Overdijk M B, Verploegen S, Ortiz Buijsse A, Vink T, Leusen J H, Bleeker W K, Parren P W. 2012. Crosstalk between human IgG isotypes and murine effector cells. J Immunol 189: 3430-8.
41. Pardo L A, Stuhmer W. 2014. The roles of K+ channels in cancer. Nature Reviews Cancer 14: 39-48.
42. Patel A J, Lazdunski M. 2004. The 2P-domain K+ channels: role in apoptosis and tumorigenesis. Pflugers Arch 448: 261-73.
43. Pei L, Wiser O, Slavin A, Mu D, Powers S, Jan L Y, Hoey T. 2003. Oncogenic potential of TASK3 (Kcnk9) depends on K+ channel function. Proc Nati Acad Sci USA 100: 7803-7807.
44. Prevarskaya N, Skryma R, Shuba Y. 2010. Ion channels and the hallmarks of cancer. Trends Mol Med 16: 107-21.
45. Queen C, Schneider W P, Selick H E, Payne P W, Landolfi N F, Duncan J F, Avdalovic N M, Levitt M, Junghans R P, Waldmann T A 1989. A humanized antibody that binds to the interleukin 2 receptor Proc. Natl. Acad. Sci. USA. 86:10029-10033.
46. Renard C B. 1999. Pharmacokinetics of heterologous and homologous immunoglobulin G, F(ab')2 and Fab after intravenous administration in the rat. J Pharmacy Pharmacology 49: 277-8.
47. Shields R L, Lai J, Keck R, O'Connell L Y, Hong K, Meng Y G, Weikert S H, Presta L G. 2002. Lack of fucose on human IgG1 N-linked oligosaccharide improves binding to human Fcgamma RIII and antibody-dependent cellular toxicity. J Biol Chem 277: 26733-40.
48. Shultz L D, Lyons B L, Burzenski L M, Gott B, Chen X, Chaleff S, Kotb M, Gillies S D, King M, Mangada J, Greiner D L, Handgretinger R. 2005. Human lymphoid and myeloid cell development in NOD/LtSz-scid IL2R gamma null mice engrafted with mobilized human hemopoietic stem cells. J Immunol. 15; 174:6477-89
49. Siegel R, Naishadham D, Jemal A. 2013. Cancer statistics. C A Cancer J Clin 63: 11-30.
50. Sun H, Luo L, Lal B, Laterra J, Li M. 2015. Probing the tumorigenic properties of two pore potassium channels using inhibitory anti-KCNK9 mAbs. Abstract. American Association for Cancer Research. April 2015, Philadelphia, Pa.
51. Sun H, Luo L, Lal B, Ma X, Chen L, Hann C L, Fulton A M, Leahy D J, Laterra J, Li M. 2016. A monoclonal antibody against KCNK9 K(+) channel extracellular domain inhibits tumour growth and metastasis. Nat Commun 7: 10339.
52. Sun J, Lu F, He H, Shen J, Messina J, Mathew R, Wang D, Sarnaik A A, Chang W C, Kim M, Cheng H, Yang S. 2014. STIM1- and Orail-mediated Ca(2+) oscillation orchestrates invadopodium formation and melanoma invasion. J Cell Biol 207: 53548.
53. Teillaud, Jean-Luc (July 2012) Antibody-dependent Cellular Cytotoxicity (ADCC). In: eLS. John Wiley & Sons, Ltd: Chichester. DOI: 10.1002'9780470015902.a0000498.pub2

54. Villalonga N, Ferreres J C, Argilés J M, Condom E, Felipe A. 2007. Potassium channels are a new target field in anticancer drug design. Recent Pat Anticancer Drug Discov 2: 212-23.

55. Walser T C, Ma X, Kundu N, Dorsey R, Goloubeva O, Fulton A M. 2007. Immune-mediated Modulation of Breast Cancer Growth and Metastasis by the Chemokine Mig (CXCL9) in a Murine Model. J Immunother 30:490-498.

56. Wang J, Xia S, Arand B, Zhu H, Machiraju R, Huang K, Ji H, Qian J. 2016. Single-Cell Co-expression Analysis Reveals Distinct Functional Modules, Co-regulation Mechanisms and Clinical Outcomes. PLoS Comput Biol 12(4):e1004892.

57. Weaver C D, Harden D, Dworetzky S I, Robertson B, Knox R J. 2004. A Thallium-Sensitive, Fluorescence-Based Assay for Detecting and Characterizing Potassium Channel Modulators in Mammalian Cells. J Biomol Screen 9: 671-677.

58. Whitsett T G, Inge L J, Dhruv H D, Cheung P Y, Weiss G J, Bremner R M, Winkles J A, Tran N L. 2013. Molecular determinants of lung cancer metastasis to the central nervous system. Transl Lung Cancer Res 2: 273-83.

59. Wonderlin W F, Woodfork K A, Strobl J S. 1995. Changes in membrane potential during the progression of MCF-7 human mammary tumor cells through the cell cycle. J Cell Physiol 165: 177-85.

60. Yamane-Ohnuki N, and Mitsuo Satoh M. 2009. Production of therapeutic antibodies with controlled fucosylation. MAbs 1:230-236.

61. Yang M, Brackenbury W J. 2013. Membrane potential and cancer progression. Front Physiol 4:185.

62. Yu B, Larrick J W. 2014a. Methods and compositions for producing double allele knock outs. WO2015010114 A1.

63. Yu B, Wages J M, Larrick J W 2014b. Antibody-membrane switch (AMS) technology for facile cell line development. Protein Eng Des Sel 27: 309-315.

64. Zhang L, Zou W, Zhou S S, Chen D D. 2009. Potassium channels and proliferation and migration of breast cancer cells. Sheng Li Xue Bao 61:15-20.

65. Zuiga R, Valenzuela C, Concha G, Brown N, Znfhiga L. 2018. TASK-3 Downregulation Triggers Cellular Senescence and Growth Inhibition in Breast Cancer Cell Lines. Int J Mol Sci 19(4). pii: E1033. doi: 10.3390/ijms19041033.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A humanized antibody or an antigen-binding fragment thereof that specifically binds to potassium two pore domain channel subfamily K member 9 (KCNK9) and that comprises:

(a) a heavy chain variable region amino acid sequence of SEQ ID NO: 9 and a light chain variable region amino acid sequence of SEQ ID NO: 15;

(b) a heavy chain variable region amino acid sequence of SEQ ID NO: 10 and a light chain variable region amino acid sequence of SEQ ID NO: 15;

(c) a heavy chain variable region amino acid sequence of SEQ ID NO: 11 and a light chain variable region amino acid sequence of SEQ ID NO: 15;

(d) a heavy chain variable region amino acid sequence of SEQ ID NO: 11 and a light chain variable region amino acid sequence of SEQ ID NO: 16;

(e) a heavy chain variable region amino acid sequence of SEQ ID NO: 12 and a light chain variable region amino acid sequence of SEQ ID NO: 15;

(f) a heavy chain variable region amino acid sequence of SEQ ID NO: 12 and a light chain variable region amino acid sequence of SEQ ID NO: 16;

(g) a heavy chain variable region amino acid sequence of SEQ ID NO: 13 and a light chain variable region amino acid sequence of SEQ ID NO: 14;

(h) a heavy chain variable region amino acid sequence of SEQ ID NO: 13 and a light chain variable region amino acid sequence of SEQ ID NO: 15; or (i) a heavy chain variable region amino acid sequence of SEQ ID NO: 13 and a light chain variable region amino acid sequence of SEQ ID NO: 16.

2. The humanized antibody or antigen-binding fragment thereof of claim 1, wherein said humanized antibody or antigen-binding fragment thereof is afucosylated.

3. The humanized antibody or antigen-binding fragment thereof of claim 2, comprising a heavy chain variable region amino acid sequence of SEQ ID NO: 13 and a light chain variable region amino acid sequence of SEQ ID NO: 15.

4. The humanized antibody or antigen-binding fragment thereof of claim 1, comprising:

(a) a heavy chain variable region amino acid sequence of SEQ ID NO: 12 and a light chain variable region amino acid sequence of SEQ ID NO: 15;

(b) a heavy chain variable region amino acid sequence of SEQ ID NO: 12 and a light chain variable region amino acid sequence of SEQ ID NO: 16;

(c) a heavy chain variable region amino acid sequence of SEQ ID NO: 13 and a light chain variable region amino acid sequence of SEQ ID NO: 15; or (d) a heavy chain variable region amino acid sequence of SEQ ID NO: 13 and a light chain variable region amino acid sequence of SEQ ID NO: 16.

5. A nucleic acid comprising a nucleotide sequence encoding the humanized antibody or antigen-binding fragment thereof of claim 1.

6. A composition comprising the humanized antibody or antigen-binding fragment thereof of claim 1 and a pharmaceutically acceptable carrier.

7. A method of inhibiting KCNK9 activity in a cell, said method comprising contacting a cell expressing KCNK9 with the humanized antibody of claim 1, whereby the humanized antibody binds to KCNK9 expressed by the cell and inhibits KCNK9 activity.

8. The method of claim 7, wherein the cell is in vitro.

9. The method of claim 7, wherein the cell is in vivo.

10. The method of claim 9, wherein the cell is in a human.

11. The method of claim 7, wherein the cell is a cancer cell.

12. The method of claim 11, wherein the cancer cell is a breast cancer cell, a lung cancer cell, or an ovarian cancer cell.

13. A method of inhibiting the growth or survival of a cancer cell, comprising contacting a cancer cell with the humanized antibody of claim 1, wherein the cancer cell expresses KCNK9.

14. The method of claim 13, wherein the cancer cell expresses KCNK9 and is present in a primary tumor.

15. The method of claim 13, wherein the cancer cell is a breast cancer cell, a lung cancer cell, or an ovarian cancer cell.

16. The method of claim 13, wherein the cancer cell is metastatic.

17. A kit comprising the humanized antibody or an antigen-binding fragment thereof of claim 1.

* * * * *

SEQUENCE LISTING

```
<160> NUMBER OF SEQ ID NOS: 16

<210> SEQ ID NO 1
<211> LENGTH: 121
<212> TYPE: PRT
<213> ORGANISM: Mus

<400> SEQUENCE: 1

Glu Val Gln Leu Gln Gln Ser Gly Pro Glu Leu Val Lys Pro Gly Ala
1               5                   10                  15

Ser Val Lys Thr Ser Cys Lys Ala Ser Gly Tyr Ser Phe Thr Gly Tyr
            20                  25                  30

Tyr Met Tyr Trp Val Lys Gln Ser Pro Glu Lys Ser Leu Glu Trp Ile
        35                  40                  45

Gly Glu Ile Asn Pro Ser Ser Gly Gly Thr Thr Tyr Asn Gln Lys Phe
    50                  55                  60
```

```
Lys Ala Lys Ala Thr Leu Thr Val Asp Lys Ser Ser Ser Thr Ala Tyr
65                  70                  75                  80

Met Gln Leu Lys Ser Leu Thr Phe Glu Asp Ser Ala Val Tyr Tyr Cys
                85                  90                  95

Ala Arg Ser Gly Leu Arg Arg Arg Phe Tyr Ala Met Asp Tyr Trp Gly
            100                 105                 110

Gln Gly Thr Ser Val Thr Val Ser Ser
        115                 120


<210> SEQ ID NO 2
<211> LENGTH: 111
<212> TYPE: PRT
<213> ORGANISM: Mus

<400> SEQUENCE: 2

Asp Ile Val Leu Thr Gln Ser Pro Ala Ser Leu Ala Val Ser Leu Gly
1               5                   10                  15

Gln Arg Ala Thr Val Ser Cys Arg Ala Ser Glu Ser Val Asp Ser Phe
            20                  25                  30

Gly Thr Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Lys Asp Pro Pro Thr Phe Gly Gly Gly Ser Lys Leu Glu Ile Lys
            100                 105                 110


<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Tyr Ser Phe Thr Gly Tyr Tyr Met Tyr
1               5


<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Glu Ile Asn Pro Ser Ser Gly Gly Thr Thr Tyr Asn Gln Lys Phe Lys
1               5                   10                  15

Ala


<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5
```

```
Ser Gly Leu Arg Arg Arg Phe Tyr Ala Met Asp Tyr
1               5                   10


<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Arg Ala Ser Glu Ser Val Asp Ser Phe Gly Thr Thr Phe Met His
1               5                   10                  15


<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Arg Ala Ser Asn Leu Glu Ser
1               5


<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Gln Gln Ser Asn Lys Asp Pro Pro Thr
1               5


<210> SEQ ID NO 9
<211> LENGTH: 121
<212> TYPE: PRT
<213> ORGANISM: Artificial Sequence
<220> FEATURE:
<223> OTHER INFORMATION: Synthetic

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met Tyr Trp Val Arg Gln Ala Pro Gly Gln Arg Leu Glu Trp Met
        35                  40                  45

Gly Glu Ile Asn Pro Ser Ser Gly Gly Thr Thr Tyr Asn Gln Lys Phe
    50                  55                  60

Lys Ala Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Leu Arg Arg Arg Phe Tyr Ala Met Asp Tyr Trp Gly
            100                 105                 110

Gln Gly Thr Leu Val Thr Val Ser Ser
        115                 120


<210> SEQ ID NO 10
<211> LENGTH: 121
```

```
<212> TYPE: PRT
<213> ORGANISM: Artificial Sequence
<220> FEATURE:
<223> OTHER INFORMATION: Synthetic

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met Tyr Trp Val Arg Gln Ala Pro Gly Gln Arg Leu Glu Trp Met
        35                  40                  45

Gly Glu Ile Asn Pro Ser Ser Gly Gly Thr Thr Tyr Asn Gln Lys Phe
    50                  55                  60

Lys Ala Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Leu Arg Arg Arg Phe Tyr Ala Met Asp Tyr Trp Gly
            100                 105                 110

Gln Gly Thr Leu Val Thr Val Ser Ser
        115                 120


<210> SEQ ID NO 11
<211> LENGTH: 121
<212> TYPE: PRT
<213> ORGANISM: Artificial Sequence
<220> FEATURE:
<223> OTHER INFORMATION: Synthetic

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met Tyr Trp Val Arg Gln Ala Pro Gly Gln Arg Leu Glu Trp Ile
        35                  40                  45

Gly Glu Ile Asn Pro Ser Ser Gly Gly Thr Thr Tyr Asn Gln Lys Phe
    50                  55                  60

Lys Ala Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Leu Arg Arg Arg Phe Tyr Ala Met Asp Tyr Trp Gly
            100                 105                 110

Gln Gly Thr Leu Val Thr Val Ser Ser
        115                 120


<210> SEQ ID NO 12
<211> LENGTH: 121
<212> TYPE: PRT
<213> ORGANISM: Artificial Sequence
<220> FEATURE:
<223> OTHER INFORMATION: Synthetic

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
```

```
            20                  25                  30

Tyr Met Tyr Trp Val Arg Gln Ala Pro Gly Gln Arg Leu Glu Trp Met
        35                  40                  45

Gly Glu Ile Asn Pro Ser Ser Gly Gly Thr Thr Tyr Asn Gln Lys Phe
    50                  55                  60

Lys Ala Arg Val Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Leu Arg Arg Arg Phe Tyr Ala Met Asp Tyr Trp Gly
            100                 105                 110

Gln Gly Thr Leu Val Thr Val Ser Ser
        115                 120


<210> SEQ ID NO 13
<211> LENGTH: 121
<212> TYPE: PRT
<213> ORGANISM: Artificial Sequence
<220> FEATURE:
<223> OTHER INFORMATION: Synthetic

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met Tyr Trp Val Arg Gln Ala Pro Gly Gln Arg Leu Glu Trp Ile
        35                  40                  45

Gly Glu Ile Asn Pro Ser Ser Gly Gly Thr Thr Tyr Asn Gln Lys Phe
    50                  55                  60

Lys Ala Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Leu Arg Arg Arg Phe Tyr Ala Met Asp Tyr Trp Gly
            100                 105                 110

Gln Gly Thr Leu Val Thr Val Ser Ser
        115                 120


<210> SEQ ID NO 14
<211> LENGTH: 111
<212> TYPE: PRT
<213> ORGANISM: Artificial Sequence
<220> FEATURE:
<223> OTHER INFORMATION: Synthetic

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Phe
            20                  25                  30

Gly Thr Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80
```

-continued

Ser Leu Glu Pro Glu Asp Phe Ala Val Tyr Tyr Cys Gln Gln Ser Asn
85 90 95

Lys Asp Pro Pro Thr Phe Gly Gly Gly Thr Lys Val Glu Ile Lys
100 105 110

<210> SEQ ID NO 15
<211> LENGTH: 111
<212> TYPE: PRT
<213> ORGANISM: Artificial Sequence
<220> FEATURE:
<223> OTHER INFORMATION: Synthetic

<400> SEQUENCE: 15

Glu Ile Val Leu Thr Gln Ser Pro Ala Thr Leu Ser Leu Ser Pro Gly
1 5 10 15

Glu Arg Ala Thr Leu Ser Cys Arg Ala Ser Glu Ser Val Asp Ser Phe
20 25 30

Gly Thr Thr Phe Met His Trp Tyr Gln Gln Lys Pro Gly Gln Ala Pro
35 40 45

Arg Leu Leu Ile Tyr Arg Ala Ser Asn Leu Glu Ser Gly Ile Pro Ala
50 55 60

Arg Phe Ser Gly Ser Gly Ser Arg Thr Asp Phe Thr Leu Thr Ile Ser
65 70 75 80

Ser Leu Glu Pro Glu Asp Phe Ala Val Tyr Tyr Cys Gln Gln Ser Asn
85 90 95

Lys Asp Pro Pro Thr Phe Gly Gly Gly Thr Lys Val Glu Ile Lys
100 105 110

<210> SEQ ID NO 16
<211> LENGTH: 111
<212> TYPE: PRT
<213> ORGANISM: Artificial Sequence
<220> FEATURE:
<223> OTHER INFORMATION: Synthetic

<400> SEQUENCE: 16

Glu Ile Val Leu Thr Gln Ser Pro Ala Thr Leu Ser Leu Ser Pro Gly
1 5 10 15

Glu Arg Ala Thr Leu Ser Cys Arg Ala Ser Glu Ser Val Asp Ser Phe
20 25 30

Gly Thr Thr Phe Met His Trp Tyr Gln Gln Lys Pro Gly Gln Pro Pro
35 40 45

Arg Leu Leu Ile Tyr Arg Ala Ser Asn Leu Glu Ser Gly Ile Pro Ala
50 55 60

Arg Phe Ser Gly Ser Gly Ser Arg Thr Asp Phe Thr Leu Thr Ile Ser
65 70 75 80

Ser Leu Glu Pro Glu Asp Phe Ala Thr Tyr Tyr Cys Gln Gln Ser Asn
85 90 95

Lys Asp Pro Pro Thr Phe Gly Gly Gly Thr Lys Val Glu Ile Lys
100 105 110